US011111216B2

(12) United States Patent
Wuest et al.

(10) Patent No.: US 11,111,216 B2
(45) Date of Patent: Sep. 7, 2021

(54) POLYCATIONIC AMPHIPHILES AS ANTIMICROBIAL AGENTS AND METHODS USING SAME

(71) Applicants: Temple University-Of The Commonwealth System of Higher Education, Philadelphia, PA (US); Villanova University, Villanova, PA (US)

(72) Inventors: William M. Wuest, Wallingford, PA (US); Kevin P. C. Minbiole, Media, PA (US)

(73) Assignees: Temple University-Of The Commonwealth System of Higher Education, Philadelphia, PA (US); Villanova University, Villanova, PA (US)

( * ) Notice: Subject to any disclaimer, the term of this patent is extended or adjusted under 35 U.S.C. 154(b) by 10 days.

(21) Appl. No.: 16/343,418

(22) PCT Filed: Oct. 26, 2017

(86) PCT No.: PCT/US2017/058409
§ 371 (c)(1),
(2) Date: Apr. 19, 2019

(87) PCT Pub. No.: WO2018/081347
PCT Pub. Date: May 3, 2018

(65) Prior Publication Data
US 2020/0277263 A1 Sep. 3, 2020

Related U.S. Application Data

(60) Provisional application No. 62/413,129, filed on Oct. 26, 2016.

(51) Int. Cl.
| *C07D 213/90* | (2006.01) |
| *A01N 33/12* | (2006.01) |
| *A01N 43/40* | (2006.01) |
| *C07C 211/63* | (2006.01) |
| *C07D 401/06* | (2006.01) |
| *C07D 401/14* | (2006.01) |

(52) U.S. Cl.
CPC ........... *C07D 213/90* (2013.01); *A01N 33/12* (2013.01); *A01N 43/40* (2013.01); *C07C 211/63* (2013.01); *C07D 401/06* (2013.01); *C07D 401/14* (2013.01)

(58) Field of Classification Search
CPC .. C07D 403/06; C07D 403/40; C07D 213/90; A01N 33/12
See application file for complete search history.

(56) References Cited

U.S. PATENT DOCUMENTS

| 3,786,058 | A | | 1/1974 | Edwards |
| 3,875,174 | A | * | 4/1975 | Edwards ............. C07D 213/16 |
| | | | | 546/265 |
| 5,744,453 | A | | 4/1998 | Mintz |
| 6,251,381 | B1 | | 6/2001 | Kourai |
| 7,410,981 | B2 | | 8/2008 | Kamiyama |
| 8,865,909 | B2 | | 10/2014 | Srebnik |
| 2013/0224258 | A1 | | 8/2013 | Baker |
| 2014/0148487 | A1 | | 5/2014 | Minbiole |
| 2016/0262384 | A1 | | 9/2016 | Wuest |
| 2016/0278375 | A1 | | 9/2016 | Wuest |
| 2018/0111893 | A1 | | 4/2018 | Wuest |

FOREIGN PATENT DOCUMENTS

| GB | 812360 | | 4/1959 |
| WO | 9937635 | | 7/1999 |
| WO | WO 2015111530 | * | 11/2015 |
| WO | 2016007821 | | 1/2016 |

OTHER PUBLICATIONS

Quagliotto et al, title:Gemini Pyridinium Surfactants: Synthesis and Conductometric Study of a Novel Class of Amphiphiles, Journal of Organic Chemistry; vol. 68; Issue 20; pp. 7651-7660. Publication Date: Sep. 11, 2003. (Year: 2003).*
Mota et al, title: The co-ordination number of transition-metal ions. Part VII. An evaluation of steric factors in the stabilization of high-spin five—co-ordinate Nickel(II) complexes of multidendate alpha-pyridyl ligands, J. Chem. Soc. (A), pp. 2036-2044; 1969.*
Alvarez-Paino et al., "Effect of glycounits on the antimicrobial properties and toxicity behavior of polymers based on quaternized D MAE MA". 2015, Biomacromolecules, 16:295-303.
Ator et al., "Beyond paraquats: Dialkyl 3, 3-and 3,4'-bipyridinium amphiphiles as antibacterial agents". 2014, Bioorg. Med. Chem. Lett. 24:3706-3709.
Ayfer et al., "Synthesis and antibacterial activities of new quaternary ammonium monomers". 2005, Des. Monomers Polym., 8:437-451.
Barbero et al., "Synthesis, Physicochemical Characterization, and Interaction with DNA of Long-Alkyl-Chain Gemini Pyridinium Surfactants". 2015, ChemPlusChem, 80:952-962.
Black et al., "TMEDA-derived biscationic amphiphiles: An economical preparation of potent antibacterial agents". 2014, Bioorg. Med. Chem. Lett., 24:99-102.
Bottcher et al., "Synthesis and activity of biomimetic biofilm disruptors". 2013, J. Am. Chem. Soc, 135:2927-2930.

(Continued)

*Primary Examiner* — Yanzhi Zhang
(74) *Attorney, Agent, or Firm* — Riverside Law LLP

(57) ABSTRACT

The present invention includes novel polycationic amphiphilic compounds useful as antimicrobial agents. The present invention further includes methods useful for removing microorganisms and/or biofilm-embedded microorganisms from a surface. The present invention further includes compositions and methods useful for preventing or reducing the growth or proliferation of microorganisms and/or biofilm-embedded microorganisms on a surface.

8 Claims, 5 Drawing Sheets

(56) References Cited

OTHER PUBLICATIONS

Bragg et al. "Bacterial Resistance to Quaternary Ammonium Compounds (QAC) Disinfectants". 2014, Infectious Diseases and Nanomedicine II, Springer India pp. 1-13.
Buffet-Bataillon et al., "Emergence of resistance to antibacterial agents: the role of quaternary ammonium compoundsa critical review". 2012, Int. J. Antimicrob. Agents, 39:381-389.
Cernakova et al., "Antimicrobial activity of berberinea constituent of Mahonia aquifolium". 2002, Folia Microbiol., 47:375-378.
Dizman et al., "Synthesis and antimicrobial activities of new water-soluble bis-quaternary ammonium methacrylate polymers". 2004, J. Appl. Polym. Sci., 94:635-642.
Dizman et al., "Synthesis and characterization of antibacterial and temperature responsive methacrylamide polymers". 2006, Macromolecules, 39:5738-5746.
Eckenhoff, et al. Dalton Transactions, 40(18), 2011, 4909-4917.
Ganewatta et al., "Bio-inspired resin acid-derived materials as anti-bacterial resistance agents with unexpected activities". 2014, Chem. Sci., 5:2011-2016.
Goswami et al., "Biocompatible Nanocarrier Fortified with a Dipyridinium-Based Amphiphile for Eradication of Biofilm". 2014, ACS Appl. Mater. Interfaces, 6:16384-16394.
Grenier et al., "The antibacterial activity of 4,4-bipyridinium amphiphiles with conventional, bicephalic and gemini architectures". 2012, Bioorg. Med. Chem. Lett., 22:4055-4058.
Holdsworth et al., "The major facilitator superfamily transporter MdtM contributes to the intrinsic resistance of *Escherichia coli* to quaternary ammonium compounds". 2013, J. Antimicrob. Chemother., 68:831-839.
Hugo, "The Mode of Action of Antibacterial Agents". 1967, J. Appl. Bacterid., 30:17-50.
Ignatova et al., "Synthesis of copolymer brushes endowed with adhesion to stainless steel surfaces and antibacterial properties by controlled nitroxide-mediated radical polymerization.". 2004, Langmuir, 20:10718-10726.
Jennings et .al., "Bioorganic Investigation of Multicationic Antimicrobials to Combat QAC-Resistant Staphylococcus aureus". 2015, ACS Inf. Dis., 1:304-309.
Jennings et al., "Quaternary ammonium compounds: an antimicrobial mainstay and platform for innovation to address bacterial resistance". 2015, ACS Inf. Dis., 1:288-303.
Jennings, MC et al., "Biofilm-Eradicating Properties of Quaternary Ammonium Amphiphiles: Simple Mimics of Antimicrobial Peptides.", ChemBioChem Communications, (2014), vol. 15, pp. 2211-2215, XP055324213.
Kenawy et al., "Biologically active polymers. V. Synthesis and antimicrobial activity of modified poly(glycidyl methacrylate-co-2-hydroxyethyl methacrylate) derivatives with quaternary ammonium and phosphonium salts". 2002, J. Polym. Sci. Part A Polym. Chem., 40:2384-2393.
Kenawy et al., "The chemistry and applications of antimicrobial polymers: a state-of-the-art review". 2007, Biomacromolecules, 8:1359-1384.
Ladow et al., "Bicephalic amphiphile architecture affects antibacterial activity". 2011, Eur. J. Med. Chem., 46:4219, 8 pages.
Lee et al., "Permanent, nonleaching antibacterial surfaces. 1. Synthesis by atom transfer radical polymerization". 2004, Biomacromolecules, 5:877-882.
Liu et al., "Nylon-3 Polymers Active against Drug-Resistant Candida albicans Biofilms". 2015, J. Am. Chem. Soc. 137:2183-2186.
LV et al., "Synthesis and evaluation of amphiphilic cationic quinine-derived for antibacterial activity against methicillin-esistant Staphylococcus aureus". 2007, Bioorg. Med. Chem. Lett., 17:4102-4106.
Martin et al., "Alkaloids from the Chinese Vine Gnetum montanum". 2011, J. Nat. Prod., 74:2425-2430.
McCormic et al., "Aqueous RAFT polymerization: recent developments in synthesis of functional water-soluble (co) polymers with controlled structures". 2004, Acc. Chem. Res., 37:312-325.

Mintzer et al., "Exploiting dendrimer multivalency to combat emerging and re-emerging infectious diseases". 2012, Mol. Pharmaceutics, 9:342-354.
Mitchell et al., "QacA Multidrug Efflux Pump fromStaphylococcus aureus: Comparative Analysis of Resistance to Diamidines, Biguanidines, and Guanylhydrazones". 1998, Antimicrob. Agents Chemother., 42:475-477.
NG et al., "Antimicrobial polycarbonates: Investigating the impact of nitrogen-containing heterocycles as quaternizing agents". 2014, Macromolecules, 47:1285-1291.
Palermo et al., "Chemical structure of cationic groups in amphiphilic polymethacrylates modulates the antimicrobial and hemolytic activities". 2009, Biomacromolecules, 10:1416-1428.
Panarin et al., "Synthesis and antimicrobial properties of polymers containing quaternary ammonium groups". 1971, khim.-Farm. Zh., 5:24-28 (English translation attached).
Paniak, TJ et al., "The antimicrobial activity of mono-, bis-, tris-, and tetracationic amphiphiles derived from simple polyamine platforms.", Bioorganic and Medicinal Chemistry Letters, (2014), vol. 24, pp. 5824-5828, XP055324209.
Poole, "Efflux-mediated antimicrobial resistance". 2005, J. Antimicrob. Chemother., 56:20-51.
Raggi et al., "Methicillin resistance, biofilm formation and resistance to benzalkonium chloride in Staphylococcus aureus clinical isolates". 2013, Clin. Microbiol., 2:1000121, 6 pages.
Ravikumar et al., "Surface-active antifungal polyquaternary amine". 2006, Biomacromolecules, 7:2762-2769.
Sidhu et al., "Frequency of Disinfectant Resistance Genes and Genetic Linkage with B-Lactamase Transposon Tn552 among Clinical Staphylococci". 2002, Antimicrob. Agents Chemother., 46:2797-2803.
Tashiro, "Antibacterial and bacterium adsorbing macromolecules". 2001, Macromol. Mater. Eng., 286:63-87.
Tew et al., "De novo design of antimicrobial polymers, foldamers, and small molecules: from discovery to practical applications". 2010, Acc. Chem. Res., 43:30-39.
Weldes in Industrial & Engineering Chemistry Product Research and Development, 9(2), 1970, 243-248.
Wimley, "Describing the mechanism of antimicrobial peptide action with the interfacial activity model". 2010, ACS Chem. Biol., 5:905-917.
Zhang et al., "Synthesis and antibacterial characterization of gemini surfactant monomers and copolymers". 2012, Polym. Chem., 3:907-913.
Abdel-Magid et al., "Reductive Amination of Aldehydes and Ketones with Sodium Triacetoxyborohydride. Studies on Direct and Indirect Reductive Amination Procedures", 1996, J. Org. Chem, 61: 3849-3862.
Chen et al., "In Vitro Antifungal Activities of Bis(Alkylpyridinium)Alkane Compounds against Pathogenic Yeasts and Molds", 2010, Antimicrob. Agents Chemother, 54: 3233-3240.
Forman et al., "Building a Better Quaternary Ammonium Compound (QAC): Branched Tetracationic Antiseptic Amphiphiles", 2016, ChemMedChem, 11: 1401-1405.
Forman et al., "Structure—Resistance Relationships: Interrogating Antiseptic Resistance in Bacteria with Multicationic Quaternary Ammonium Dyes", 2016, ChemMedChem, 11: 958-962.
Fromherz et al., "Pharmacological effects of (beta-pyridylcarbinol (Niacol Roche) and related beta-pyridyl compounds", 1948, Helv. Physiol. Pharmacol. Acta, 6:42-54.
Gilbert et al., "Cationic antiseptics: diversity of action under a common epithet", 2005, J. Appl. Microbiol, 99: 703-715.
Haley, "Review of the toxicology of paraquat (1,1'-dimethyl-4,4'-bipyridinium chloride)", 1979, Clin. Toxicol, 14: 1-46.
Hartley, "The Critical Concentration for Micelles in Solutions of Cetane Sulfonic Acid", 1936, J. Am. Chem. Soc, 58: 2347-2354.
Hübner et al., "Review on the efficacy, safety and clinical applications of polihexanide, a modern wound antiseptic", 2010, A. Kramer, Skin Pharmacol. Physiol, 23: 17-27.
Jenkins et al., "A comparison of cetylpyridinium chloride, triclosan and chlorhexidine mouthrinse formulations for effects on plaque regrowth", 1994, M. Addy, R. G. Newcombe, J. Clin. Periodontol, 21: 441-444.

(56) References Cited

OTHER PUBLICATIONS

Kahner et al., "New types of self-organizing interfacial alginate membranes", 2010, Colloid Polymer Sci, 288: 461-468.

Milstone et al., "Chlorhexidine: expanding the armamentarium for infection control and prevention", 2008, Clin. Infect. Dis, 46: 274-281.

Minbiole et al., "From antimicrobial activity to mechanism of resistance: the multifaceted role of simple quaternary ammonium compounds in bacterial eradication", 2016, Tetrahedron, 72: 3559-3566.

Mitchell et al., "Scaffold☐Hopping of Multicationic Amphiphiles Yields Three New Classes of Antimicrobials", 2015, ChemBioChem, 16: 2299-2303.

Obando et al., "Synthesis, antifungal, haemolytic and cytotoxic activities of a series of bis(alkylpyridinium)alkanes", 2009, Bioorg. Med. Chem, 17: 6329-6339.

Oh et al., "Colloids Produced by Simple Self-Assembly of Inorganic Tennis Balls and Nonrigid Polypyridyl Ligands", 2007, Bull. Korean Chem. Soc. 28:2193-2194.

Yang et al., "Enhanced removal of bisphenol A from aqueous solution by organo-montmorillonites modified with novel Gemini pyridinium surfactants containing long alkyl chain", 2016, Chem. Eng. J. 2016, 285: 27-38.

\* cited by examiner

POLYCATIONIC AMPHIPHILES AS ANTIMICROBIAL AGENTS AND METHODS USING SAME

CROSS-REFERENCE TO RELATED APPLICATIONS

The present application a U.S. national phase application filed under 35 U.S.C. § 371 claiming priority to International Patent Application No. PCT/US17/58409, filed Oct. 26, 2017, which is entitled to priority under 35 U.S.C. § 119(e) to U.S. Provisional Patent Application No. 62/413,129, filed Oct. 26, 2016, which is incorporated by reference herein in its entirety.

BACKGROUND OF THE INVENTION

Quaternary ammonium compounds (QACs) are a staple of modern antiseptics, and are featured in a bevy of industrial and consumer products (Walker et al., 2002, D. Paulson, Quaternary Ammonium Compounds, Marcel Dekker, New York). In QACs, the cationic nitrogen atom is attracted to the net anionic charge of the bacterial cell membrane, offering the promise of preferential destruction of prokaryotic cells over their eukaryotic counterparts. Attachment serves as a prelude to cell lysis, which is effected by the insertion of the non-polar tail(s) of the QAC into the bacterial cell membrane, leading to loss of cell integrity (Gilbert et al., 2005, J. Appl. Microbiol, 99: 703-715). Previous studies investigated the advantages of multicationic QACs (multiQACs), species with multiple cationic groups as well as multiple non-polar tails. This has led to the assembly of hundreds of novel structures and, more importantly, elucidation of numerous lessons of both structure-activity and structure-resistance relationships of QAC amphiphiles (Minbiole et al., 2016, Tetrahedron, 72: 3559-3566, Forman et al., 2016, ChemMedChem, 11: 1401-1405, Forman et al., 2016, ChemMedChem, 11: 958-962, Mitchell et al., 2015, ChemBioChem, 16: 2299-2303, Jennings et al., 2015, ACS Inf Dis, 1: 304-308, Paniak et al., 2014, Bioorg. Med. Chem. Lett, 24: 5824-5828, Ator et al., 2014, Bioorg. Med. Chem. Lett, 24: 3706-3709, Jennings et al., 2014, ChemBioChem, 15: 2211-2215, Black et al., 2014, Bioorg. Med. Chem. Lett, 24: 99-102, Grenier et al., 2012, Bioorg. Med. Chem. Lett, 22: 4055-4058).

There exist, however, classes of QACs whose cationic charge is not strictly localized. For example, chlorhexidine (CHX) is a bisbiguanide QAC often found in mouthwashes and cosmetics; cationic charge is spread across the five nitrogen atoms of the biguanide group, which is protonated at neutral pH (Milstone et al., 2008, Clin. Infect. Dis, 46: 274-281. Polymeric analogs include polyhexanide, a water-soluble polybiguanide used in swimming pools and surgical dressings (Hubner et al., 2010, A. Kramer, Skin Pharmacol. Physiol, 23: 17-27). The common antiseptic cetylpyridinium chloride (CPC), originally reported in the 1930's, is similarly found in many mouthwashes and other consumer products (Hartley et al., 1936, J. Am. Chem. Soc, 58: 2347-2354, FR Patent No. 812360, Jenkins et al., 1994, M. Addy, R. G. Newcombe, J. Clin. Periodontol, 21: 441-444), and its cationic charge is spread over the entirety of the pyridinium ring. Polymeric species such as polyvinyl pyridine also derive efficacy from pyridine residues whose protonation is pH-dependent.

There are numerous examples of multiQACs that rely on non-localized charges, and the application of directly-connected multi-pyridyl compounds in bioactive molecules is well precedent. For example, paraquat (N,N'-dimethyl-4,4'-bispyridinium dichloride) is a well-known herbicide based on the 4,4'-bispyridine core (Haley et al., 1979, Clin. Toxicol, 14: 1-46); the development of a number of long-chained analogs to this structure, exploring advantages of asymmetry (Grenier et al., 2012, Bioorg. Med. Chem. Lett, 22: 4055-4058) and differing orientations (Ator et al., 2014, Bioorg. Med. Chem. Lett, 24: 3706-3709) of the core bispyridine structure has been done. Conversely, unconjugated multi-pyridyl compounds are not as well reported. Some have been designed to possess significant spacing between the pyridinium residues (U.S. Pat. No. 3,786,058, Quagliotto et al., 2003, J. Org. Chem, 68: 7651-7660, Barbero et al., 2015, ChemPlusChem, 80: 952-962); others are based on the alkylation of simple bis-pyridine cores (Kahner et al., 2010, Colloid Polymer Sci, 288: 461-468, Yang et al., 2016, Chem. Eng. J. 2016, 285: 27-38. A third class of structures utilize a bis-alkyl halide starting core, then exploit alkyl pyridine nucleophiles to functionalize the ends of the chain, resulting in bis-pyridinium compounds (Obando et al., 2009, Bioorg. Med. Chem, 17: 6329-6339, Chen et al., 2010, Antimicrob. Agents Chemother, 54: 3233-3240). A small number of compounds have two unconjugated pyridinium moieties, which seem to outperform similar antiseptic amphiphiles (Minbiole et al., 2016, Tetrahedron, 72: 3559-3566).

There is a continuing need in the art for novel antimicrobial agents with low toxicity profiles that also demonstrate activity against resistant bacterial strains. The present invention addresses this unmet need in the art.

SUMMARY OF THE INVENTION

The present invention includes a compound selected from the group consisting of formula I-IV:

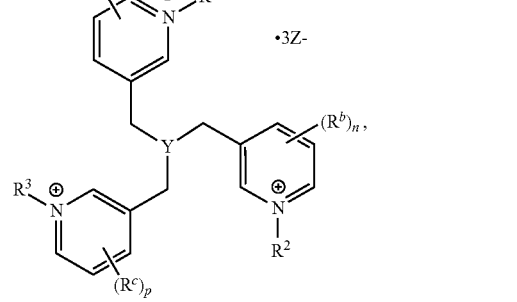

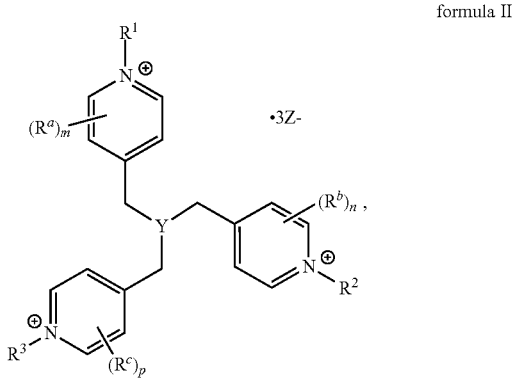

-continued

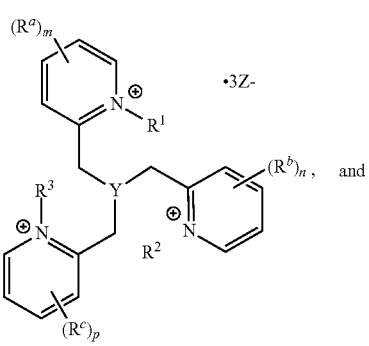

formula III

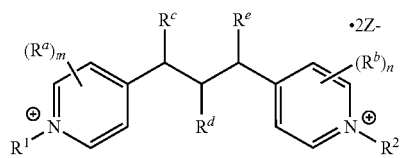

formula IV wherein in formula I-IV:

$R^1$, $R^2$, and $R^3$ are each independently selected from the group consisting of null, H or $C_1$-$C_{25}$ alkyl, wherein the alkyl group may be optionally substituted with —OR', —NR'$_2$, —NR'—C(O)R', —C(O)NR'$_2$, —NR'—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl, further wherein the alkyl group may optionally be interrupted with a —O—C(O)— group or a —C(O)O— group;

each occurrence of $R^a$, $R^b$, $R^c$, $R^d$, and $R^e$ is independently selected from the group consisting of H, $C_1$-$C_6$ alkyl, —OR', —CN, —NO$_2$, —NR'$_2$, —N—C(O)R', —C(O)NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and $C_{1-4}$ alkyl;

Y is N or CR'';

R'' is H or $C_1$-$C_6$ alkyl, wherein the alkyl group may be optionally substituted and may combine with any of $R^a$, $R^b$, and $R^c$ to form a ring;

each occurrence of Z is independently a counterion;

m is an integer from 0 to 4;

n is an integer from 0 to 4; and p is an integer from 0 to 4

In one embodiment, at least one of $R^1$, $R^2$, and $R^3$ is $C_8$ alkyl. In one embodiment, at least one of $R^1$, $R^2$, and $R^3$ is $C_{10}$ alkyl. In one embodiment, at least one of $R^1$, $R^2$, and $R^3$ is $C_{11}$ alkyl. In one embodiment, at least one of $R^1$, $R^2$, and $R^3$ is $C_{12}$ alkyl. In one embodiment, at least one of $R^1$, $R^2$, and $R^3$ is $C_{13}$ alkyl. In one embodiment, at least one of $R^1$, $R^2$, and $R^3$ is $C_{14}$ alkyl. In one embodiment, at least one of $R^1$, $R^2$, and $R^3$ is $C_{16}$ alkyl. In one embodiment, at least one of $R^1$, $R^2$, and $R^3$ is $C_{18}$ alkyl. In one embodiment, the $C_1$-$C_{25}$ alkyl group is selected from the group consisting of —$R^4$—O—C(O)—$R^5$ and —$R^4$—(O)C—O—$R^5$, wherein $R^4$ and $R^5$ are each independently an optionally substituted alkyl chain, provided that the total number of carbon atoms in the alkyl chains of $R^4$ and $R^5$ is 4 to 25 carbon atoms. In one embodiment, Z is Br$^-$. In one embodiment, $R^1$, $R^2$, and $R^3$ are each $C_8$-$C_{18}$ alkyl.

In one embodiment, the compound is selected from the group consisting of:

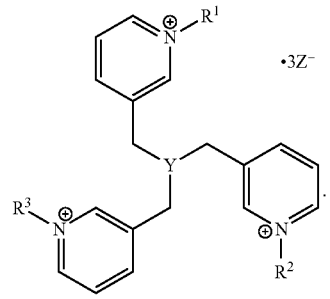

M3Pyr-8,8,8 – $R^1$, $R^2$, $R^3$ = $C_8H_{17}$
M3Pyr-10,10,10 – $R^1$, $R^2$, $R^3$ = $C_{10}H_{21}$
M3Pyr-11,11,11 – $R^1$, $R^2$, $R^3$ = $C_{11}H_{23}$
M3Pyr-12,12,12 – $R^1$, $R^2$, $R^3$ = $C_{12}H_{25}$
M3Pyr-13,13,13 – $R^1$, $R^2$, $R^3$ = $C_{13}H_{27}$
M3Pyr-14,14,14 – $R^1$, $R^2$, $R^3$ = $C_{14}H_{29}$
M3Pyr-16,16,16 – $R^1$, $R^2$, $R^3$ = $C_{16}H_{33}$
M3Pyr-18,18,18 – $R^1$, $R^2$, $R^3$ = $C_{18}H_{37}$

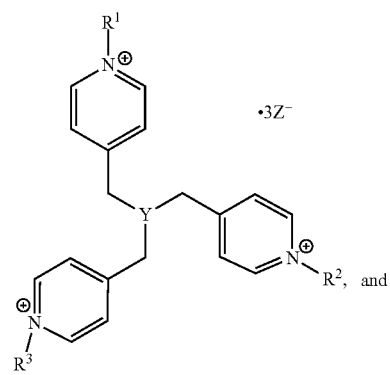

P3Pyr-8,8,8 – $R^1$, $R^2$, $R^3$ = $C_8H_{17}$
P3Pyr-10,10,10 – $R^1$, $R^2$, $R^3$ = $C_{10}H_{21}$
P3Pyr-11,11,11 – $R^1$, $R^2$, $R^3$ = $C_{11}H_{23}$
P3Pyr-12,12,12 – $R^1$, $R^2$, $R^3$ = $C_{12}H_{25}$
P3Pyr-13,13,13 – $R^1$, $R^2$, $R^3$ = $C_{13}H_{27}$
P3Pyr-14,14,14 – $R^1$, $R^2$, $R^3$ = $C_{14}H_{29}$
P3Pyr-16,16,16 – $R^1$, $R^2$, $R^3$ = $C_{16}H_{33}$
P3Pyr-18,18,18 – $R^1$, $R^2$, $R^3$ = $C_{18}H_{37}$

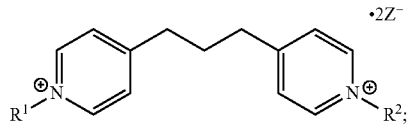

2Pyr-8,8 – $R^1$, $R^2$ = $C_8H_{17}$
2Pyr-10,10 – $R^1$, $R^2$ = $C_{10}H_{21}$
2Pyr-11,11 – $R^1$, $R^2$ = $C_{11}H_{23}$
2Pyr-12,12 – $R^1$, $R^2$ = $C_{12}H_{25}$
2Pyr-13,13 – $R^1$, $R^2$ = $C_{13}H_{27}$
2Pyr-14,14 – $R^1$, $R^2$ = $C_{14}H_{29}$
2Pyr-16,16 – $R^1$, $R^2$ = $C_{16}H_{33}$
2Pyr-18,18 – $R^1$, $R^2$ = $C_{18}H_{37}$ wherein each occurrence of Z is independently selected from the group consisting of I$^-$ and Br$^-$.

In one embodiment, the compound of formula IV is 2Pyr-11,11:

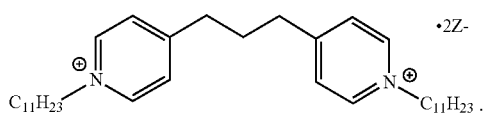

In one embodiment, the at least one compound is attached to a second compound or moiety. In one embodiment, the second compound or moiety is selected from the group consisting of a QAC, an antimicrobial peptide, a sugar, an iron siderophore, a solid surface, a poly(alkyl ether), and a nucleophilic residue.

The present invention also includes a composition comprising a compound of the invention. In one embodiment, the composition is an antimicrobial composition.

The present invention also includes a method for preventing or reducing the growth or proliferation of microorganisms or biofilm-embedded microorganisms on at least one surface. In one embodiment, the method includes the steps of providing at least one surface, providing a composition comprising at least one compound of the invention, and contacting the at least one surface with the composition in an amount sufficient to prevent or reduce the growth or proliferation of microorganisms or biofilm-embedded microorganisms on the at least one surface.

In one embodiment, the composition further comprises a base material. In one embodiment, the composition further comprises at least one additional antimicrobial agent. In one embodiment, wherein the at least one compound of the invention and the at least one additional antimicrobial agent act synergistically to prevent or reduce the growth or proliferation of microorganisms or biofilm-embedded microorganisms on the at least one surface. In one embodiment, the composition is contacted with the at least one surface for a period of time sufficient to form a coating of the composition on the at least one surface. In one embodiment, the surface is a subject's body. In one embodiment, the surface is a solid surface.

The present invention also includes a method for removing at least a portion of or reducing the number of microorganisms or biofilm-embedded microorganisms attached to at least one surface. In one embodiment, the method includes the steps of providing at least one surface, wherein the microorganisms or biofilm-embedded microorganisms are attached to the at least one surface, providing a composition comprising at least one compound of the invention, and contacting the composition with the at least one surface in an amount sufficient to remove at least a portion of or reduce the number of microorganisms or biofilm-embedded microorganisms attached to the at least one surface.

In one embodiment, the composition further comprises a base material. In one embodiment, the composition further comprises at least one additional antimicrobial agent. In one embodiment, the at least one compound of claim 1 and the at least one additional antimicrobial agent act synergistically to reduce or prevent the growth or proliferation of microorganisms or biofilm-embedded microorganisms on the at least one surface. In one embodiment, the composition is contacted with the at least one surface for a period of time sufficient to form a coating of the composition on the at least one surface. In one embodiment, the surface is a subject's body. In one embodiment, the surface is a solid surface.

The present invention also includes a film or coating comprising at least one compound of the invention.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1B is an image of pyridinium antiseptics.

DETAILED DESCRIPTION

Figure 1A:
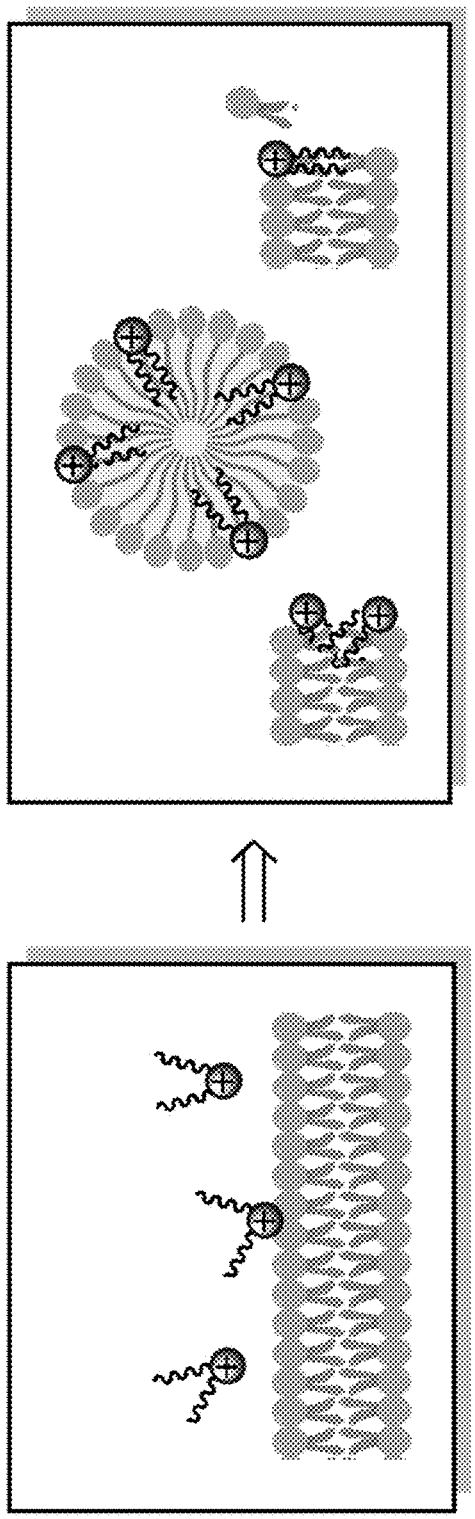
FIGS. 1A-1B, is an image depicting the mechanism of action of QACs wherein cationic head group(s) are shown in red and hydrophobic tail(s) in black (FIG. 1A).

The present invention includes novel polycationic amphiphilic compounds that are useful as antimicrobial agents. In one embodiment, the compounds are quaternary ammonium compounds (QACs). In one embodiment, the polycationic amphiphilic compounds are multicationic quaternary ammonium compounds (multiQACs). The present invention also includes methods of using the compounds of the invention for preventing or reducing the growth or proliferation of microorganisms or biofilm-embedded microorganisms on at least one surface. The present invention also includes a method for removing at least a portion of or reducing the number of microorganisms or biofilm-embedded microorganisms attached to at least one surface using the compounds of the invention.

Definitions

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated, or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

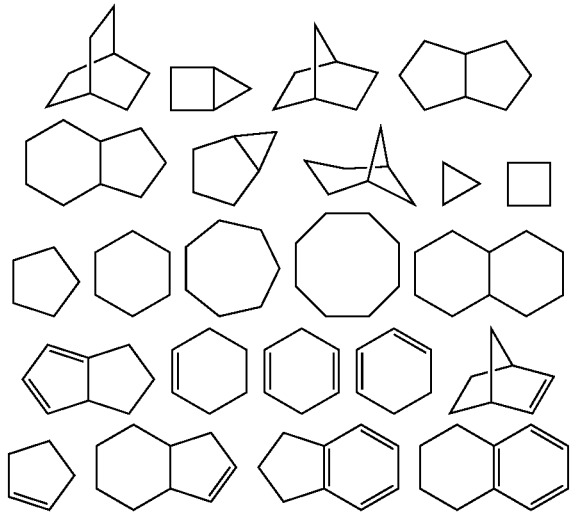

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "aromatic" refers to a carbocycle or heterocycle with one or more polyunsaturated rings and having aromatic character, i.e. having (4n+2) delocalized π (pi) electrons, where n is an integer.

The terms "aryl" or "arylene" are used interchangeably herein, and when employed alone or in combination with other terms, mean, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is one of aryl-$CH_2$—, aryl-CH($CH_3$)—, and aryl-$CH_3$. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "benzylic hydrogen" refers to a hydrogen atom bound to a carbon atom that is directly bound to an aromatic ring. Benzylic methyl, benzylic methylene, and benzylic methine all contain at least one benzylic hydrogen.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —$NH_2$, —OH, —NH($CH_3$), —N($CH_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, the term "antimicrobial" refers to an ability to kill or inhibit the growth of microorganisms, including but not limited to bacteria, viruses, yeast, fungi, and protozoa, or to attenuate the severity of a microbial infection. The antimicrobial compounds or compositions of the present invention are compounds or compositions that may be used for cleaning or sterilization, or may be used in the treatment of disease and infection. The applications may include both in vitro and in vivo antimicrobial uses. "Applying" an antimicrobial composition may include administrating a composition into a human or animal subject.

As used herein, a "microorganism" refers to any microorganism that may colonize or proliferate on the surface including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, the term "biofilm" refers to a film formed by a group of microorganisms adhered together. The term "antibiofilm" as used herein refers to an ability to kill, disperse and/or eradicate a pre-established biofilm.

As used herein, the term "contacting" includes, but is not limited to, impregnating, compounding, mixing, integrating, coating, rubbing, painting, spraying, immersing, rolling, smearing and dipping.

As used herein, the term "treatment" or "treating," is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of medicine or pharmacology. In one embodiment, the condition is selected from the group consisting of a bacterial infection, fungal infection, mycobacterial infection, viral infection, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "pharmaceutical composition" refers to a mixture of at least one compound useful within the invention with a pharmaceutically acceptable carrier. The pharmaceutical composition facilitates administration of the compound to a patient or subject, or use of the compound within the methods of the invention. Multiple techniques of administering a compound exist in the art including, but not limited to, intravenous, oral, aerosol, parenteral, ophthalmic, pulmonary and topical administration.

As used herein, the terms "effective amount," "pharmaceutically effective amount" and "therapeutically effective amount" refer to a non-toxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Effective amount" also refers to a sufficient amount of the polycationic amphiphile to prevent or reduce the growth or proliferation of microorganisms and/or biofilm-embedded microorganisms on a surface, in the case of the composition being a coating. "Effective amount" also refers to a sufficient amount of the polycationic amphiphile to penetrate, or break-up, at least a portion of the biofilm on a surface, thereby facilitating access of polycationic amphiphile, antimicrobial agent, and/or antifungal agent to the microorganisms embedded in the biofilm, thus removing at least a portion of or reducing the number of microorganisms attached to a surface. The amount may vary for each compound considered within the compositions of the invention, and upon known factors such as the pharmaceutical characteristics, type of surface, degree of biofilm-embedded microorganism contamination, and the use and length of use. It is within the ability of a person of ordinary skill in the art to relatively easily determine an effective concentration for each compound considered within the compositions of the invention.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, ammonium, sodium and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

As used herein, a "biofilm-embedded microorganism" refers to any microorganism that forms or nests within a biofilm during colonization and proliferation on a surface, including, but not limited to, gram-positive bacteria (such as *Staphylococcus epidermidis*), gram-negative bacteria (such as *Pseudomonas aeruginosa*), mycobacteria (such as *Mycobacterium tuberculosis*), fungi (such as *Candida albicans*), or virus.

As used herein, the term "minimum inhibitory concentration (MIC)" refers to the lowest concentration of an antimicrobial agent that will inhibit the visible growth of a microorganism after overnight incubation. MIC values against bacteria, for example, the Gram-positive *Staphylococcus aureus* and *Enterococcus faecalis* and the Gram-negative *Escherichia coli* and *Pseudomonas aeruginosa* were determined by standard methods. See also P. A. Wayne, Methods for Dilution Antimicrobial Tests for Bacteria that Grow Aerobically; Approved Standard, Ninth Edition, 2012, CLSI Document M07-A9, Vol. 32 No. 2, which is incorporated by reference herein in its entirety.

As used herein, the term "the minimum biofilm eradication concentration (MBEC)" of a compound refers to the lowest concentration of compound dosed against a previously established bacterial biofilm that leads to a clear well (optical density of less than 0.1) when the treated biofilm is regrown in fresh media, indicating >95% clearance of bacteria. A regrowth assay was used to establish the MBEC of a compound to evaluate the antibiofilm activity. See also H. Ceri, M. Olson, D. Morck, D. Storey, R. Read, A. Buret, B. Olson, *Methods Enzymol.* 2001, 337, 377, which is incorporated by reference herein in its entirety.

As used herein, the term "organic solvent" refers to solvents including, but not limited to, alcohols (e.g., methanol and ethanol), ketones (e.g., acetone and methylethylketone), ethers (e.g., tetrahydrofuran), aldehydes (e.g., formaldehyde), acetonitrile, carboxylic acids (e.g., formic acid and acetic acid), methylene chloride, chloroform, alkyl carbonates, and hydrocarbons (e.g., hexane and heptane, and xylene), esters (e.g., ethyl acetate, propyl acetate, butyl acetate, amyl acetate, and combination thereof) or similar solvents.

As used herein, the term "alkalinizing agent" refers to an organic and inorganic base, including sodium hydroxide, potassium hydroxide, alkyl hydroxides, ammonia in water (27% ammonium hydroxide), diethylamine and triethylamine.

As used herein, the term "high ionic strength salt" refers to a salt exhibiting high ionic strength, such as sodium chloride, potassium chloride, or ammonium acetate. These salts may act both as an alkalinizing agent and as a penetrating agent to enhance the reactivity of the surface. Therefore, in one specific embodiment, high ionic strength salts may also be used in the step of forming the biofilm-penetrating composition.

As used herein, the term "base material" refers to any material that effectively disperses the polycationic amphiphile at an effective concentration to contact the microorganisms and/or penetrate or disrupt the biofilm. The base material thus facilitates access of the polycationic amphiphile, antimicrobial agent, and/or antifungal agent to the microorganisms on the surface and/or embedded in the biofilm, thus removing at least a portion of or reducing the number of microorganisms attached to a surface. The term "base material" also includes any solution that effectively disperses the polycationic amphiphile at an effective concentration to form a composition coating for a surface, which prevents or reduces the growth or proliferation of microorganisms and/or biofilm-embedded microorganisms on a surface. In the case of the composition coating, the base material may also facilitate the adhesion of the composition to a surface, thus preventing the composition coating from being easily removed from the surface.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This definition applies regardless of the breadth of the range.

Description

The present invention is based in part on the discovery that novel multicationic quaternary ammonium compounds (QACs) do not show diminished activity against QAC-resistant bacterial strains, and are in fact equipotent against both sensitive and resistant strains. These compounds also show significant advantages over the monocationic CPC; activity against both Gram-negative bacteria and resistant MRSA strains and have excellent toxicity profiles. Thus, the present invention provides novel polycationic compounds that may be useful as antimicrobial agents and methods of use thereof. In one embodiment, the multiQAC contains two or three cations. The present invention also includes a composition comprising at least one compound of the invention.

Figure 1B:
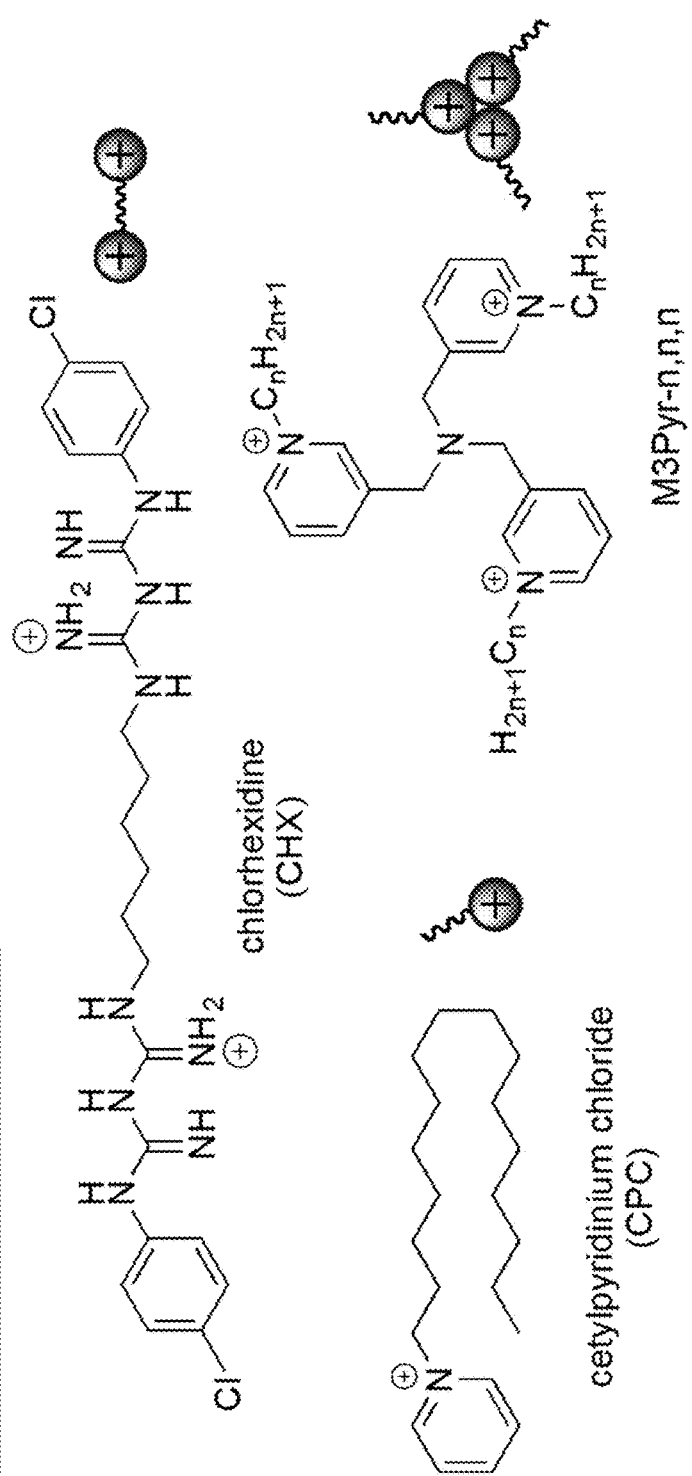

Examples of common QACs, such as chlorhexidine and cetylpyridinium chloride, are shown in FIG. 1. A mechanism of action of QACs is also depicted in FIG. 1. While these QAC structures are regarded as reasonably non-toxic, as many can be directly applied to human skin or even used in oral therapies, it is now recognized that many known compounds are likely to be susceptible to bacterial resistance.

The compounds of the invention are structurally distinct from commercialized QACs. While traditional QACs bear one or occasionally two cations, and thus are vulnerable to QAC resistance genes, the compounds of the invention may contain bis- or triscationic structures. Despite numerous reports of the antimicrobial activity of biscationic amphiphiles, no investigations correlating antimicrobial activity to amphiphiles with three quaternary ammonium groups were found. This stood in stark contrast to the wide variety of bioactive natural products (and derivatives thereof) incorporating multiple primary, secondary, and tertiary amines.

In one embodiment, the compounds of the invention demonstrate biofilm eradication against both Gram-positive and Gram-negative bacteria. In another embodiment, the compounds of the invention contain a wide array of architectures of polycationic structures, and can be prepared by straightforward synthetic routes. In another embodiment, the compounds of the invention demonstrate "resistance to resistance" in MRSA multi-generational tests. In another embodiment, the compounds of the invention demonstrate effectiveness against the *Staphylococcus aureus* (SA), *Enterococcus faecalis* (EF), *Escherichia coli* (EC), and *Pseudomonas aeruginosa* (PA), community-acquired methicillin-resistant SA (CA-MRSA), hospital-acquired methicillin-resistant SA (HA-MRSA), which are pathogens of highest clinical concern.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is at least one compound selected from the group consisting of formula I-IV:

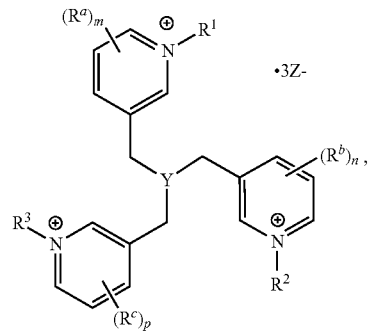

formula I

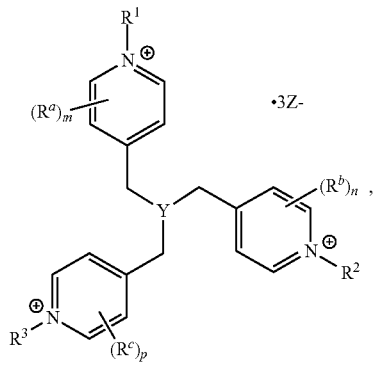

formula II

-continued

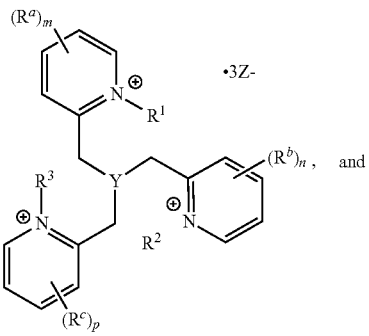
formula III

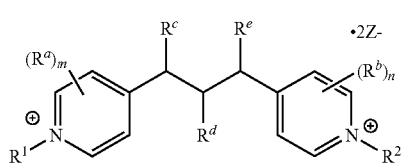
formula IV wherein in formula I-IV:
R$^1$, R$^2$, and R$^3$ are each independently selected from the group consisting of null, H or C$_1$-C$_{25}$ alkyl, wherein the alkyl group may be optionally substituted with —OR', —NR'$_2$, —NR'—C(O)R', —C(O)NR'$_2$, —NR'—C(O)CR'=CR', —SR', —O—C(O)R', —C(O)OR', —C(O)R', —CF$_3$, —OCF$_3$, halogen, benzyl, o-vinylbenzyl, m-vinylbenzyl, p-vinylbenzyl, phenyl, allyl, and substituted allyl, further wherein the alkyl group may optionally be interrupted with a —O—C(O)— group or a —C(O)O— group;

each occurrence of R$^a$, R$^b$, R$^c$, R$^d$, and W is independently selected from the group consisting of H, C$_1$-C$_6$ alkyl, —OR', —CN, —NO$_2$, —NR'$_2$, —N—C(O)R', —C(O)NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and C$_{1-4}$ alkyl;

Y is N or CR";

R" is H or C$_1$-C$_6$ alkyl, wherein the alkyl group may be optionally substituted and may combine with any of W, R$^b$, and R$^c$ to form a ring;

each occurrence of Z is independently a counterion;

m is an integer from 0 to 4;

n is an integer from 0 to 4; and p is an integer from 0 to 4.

In one embodiment, the compound is a compound of formula I. In another embodiment, the compound is a compound of formula II. In another embodiment, the compound is a compound of formula III. In another embodiment, the compound is a compound of formula IIV.

In one embodiment, at least one of R$^1$, R$^2$, and R$^3$ is C$_8$-C$_{18}$ alkyl. In one embodiment, at least one of R$^1$, R$^2$ and R$^3$, is C$_8$ alkyl. In one embodiment, at least one of R$^1$, R$^2$ and R$^3$, is Cm alkyl. In one embodiment, at least one of R$^1$, R$^2$ and R$^3$, is Cu alkyl. In one embodiment, at least one of R$^1$, R$^2$ and R$^3$, is C$_{12}$ alkyl. In one embodiment, at least one of R$^1$, R$^2$ and R$^3$, is C$_{13}$ alkyl. In one embodiment, at least one of R$^1$, R$^2$ and R$^3$, is C$_{14}$ alkyl. In one embodiment, at least one of R$^1$, R$^2$ and R$^3$, is C$_{16}$ alkyl.

In one embodiment, at least one of R$^1$ and R$^2$ is —C$_8$-C$_{18}$ alkyl. In one embodiment, at least one of R$^1$ and R$^2$ is C$_8$ alkyl. In one embodiment, at least one of R$^1$ and R$^2$ is C$_{10}$ alkyl. In one embodiment, at least one of R$^1$ and R$^2$ is C$_{11}$ alkyl. In one embodiment, at least one of R$^1$ and R$^2$ is C$_{12}$ alkyl. In one embodiment, at least one of R$^1$ and R$^2$ is C$_{13}$ alkyl. In one embodiment, at least one of R$^1$ and R$^2$ is C$_{14}$ alkyl. In one embodiment, at least one of R$^1$ and R$^2$ is C$_{16}$ alkyl.

In one embodiment, each of R$^1$, R$^2$, and R$^3$ is C$_8$-C$_{18}$ alkyl. In one embodiment, each of R$^1$, R$^2$ and R$^3$, is C$_8$ alkyl. In one embodiment, each of R$^1$, R$^2$ and R$^3$, is C$_{10}$ alkyl. In one embodiment, each of R$^1$, R$^2$ and R$^3$, is C$_{11}$ alkyl. In one embodiment, each of R$^1$, R$^2$ and R$^3$, is C$_{12}$ alkyl. In one embodiment, each of R$^1$, R$^2$ and R$^3$, is C$_{13}$ alkyl. In one embodiment, each of R$^1$, R$^2$ and R$^3$, is C$_{14}$ alkyl. In one embodiment, each of R$^1$, R$^2$ and R$^3$, is C$_{16}$ alkyl.

In one embodiment, each of R$^1$ and R$^2$ is C$_8$-C$_{18}$ alkyl. In one embodiment each of R$^1$ and R$^2$ is C$_8$ alkyl. In one embodiment, each of R$^1$ and R$^2$ is C$_{10}$ alkyl. In one embodiment, each of R$^1$ and R$^2$ is C$_{11}$ alkyl. In one embodiment, each R$^1$ and R$^2$ is C$_{12}$ alkyl. In one embodiment, each of R$^1$ and R$^2$ is C$_{13}$ alkyl. In one embodiment each of R$^1$ and R$^2$ is C$_{14}$ alkyl. In one embodiment, each of R$^1$ and R$^2$ is C$_{16}$ alkyl.

In some embodiments, the C$_1$-C$_{25}$ alkyl group may optionally be interrupted with a —O—C(O)— group or a —C(O)O— group. In one embodiment, the C$_1$-C$_{25}$ alkyl group is selected from the group consisting of —R$^4$—O—C(O)—R$^5$ and —R$^4$—(O)C—O—R$^5$, wherein R$^4$ and R$^5$ are each independently an optionally substituted alkyl chain, provided that the total number of carbon atoms in the alkyl chains of R$^4$ and R$^5$ is 4 to 25 carbon atoms. In another embodiment, the C$_1$-C$_{25}$ alkyl group is selected from the group consisting of —(CH$_2$)$_x$—O—C(O)—(CH$_2$)$_y$—CH$_3$ and —(CH$_2$)$_x$—C(O)—O—(CH$_2$)$_y$—CH$_3$, wherein x and y are each independently an integer between 0 and 24, provided that x+y is an integer from 4 to 24.

In one embodiment, Z is selected from the group consisting of a halogen ion, a mesylate ion, a tosylate ion, triflate ion, an acetate ion, a propionate ion, and a stearate ion. In one embodiment, Z is a halogen ion. In one embodiment, Z is Br.

In one embodiment, the compound of the invention is selected from the group consisting of:

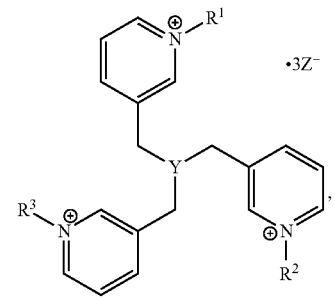

M3Pyr-8,8,8 – R$^1$, R$^2$, R$^3$ = C$_8$H$_{17}$
M3Pyr-10,10,10 – R$^1$, R$^2$, R$^3$ = C$_{10}$H$_{21}$
M3Pyr-11,11,11 – R$^1$, R$^2$, R$^3$ = C$_{11}$H$_{23}$
M3Pyr-12,12,12 – R$^1$, R$^2$, R$^3$ = C$_{12}$H$_{25}$
M3Pyr-13,13,13 – R$^1$, R$^2$, R$^3$ = C$_{13}$H$_{27}$
M3Pyr-14,14,14 – R$^1$, R$^2$, R$^3$ = C$_{14}$H$_{29}$
M3Pyr-16,16,16 – R$^1$, R$^2$, R$^3$ = C$_{16}$H$_{33}$
M3Pyr-18,18,18 – R$^1$, R$^2$, R$^3$ = C$_{18}$H$_{37}$

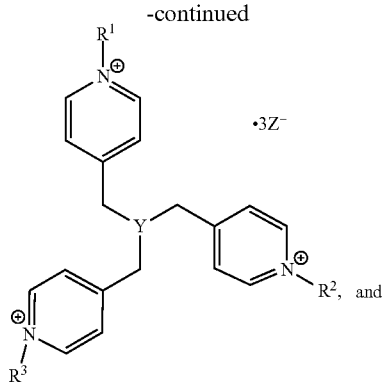

P3Pyr-8,8,8 – $R^1, R^2, R^3 = C_8H_{17}$
P3Pyr-10,10,10 – $R^1, R^2, R^3 = C_{10}H_{21}$
P3Pyr-11,11,11 – $R^1, R^2, R^3 = C_{11}H_{23}$
P3Pyr-12,12,12 – $R^1, R^2, R^3 = C_{12}H_{25}$
P3Pyr-13,13,13 – $R^1, R^2, R^3 = C_{13}H_{27}$
P3Pyr-14,14,14 – $R^1, R^2, R^3 = C_{14}H_{29}$
P3Pyr-16,16,16 – $R^1, R^2, R^3 = C_{16}H_{33}$
P3Pyr-18,18,18 – $R^1, R^2, R^3 = C_{18}H_{37}$

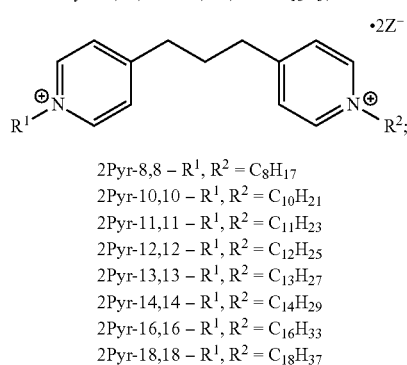

2Pyr-8,8 – $R^1, R^2 = C_8H_{17}$
2Pyr-10,10 – $R^1, R^2 = C_{10}H_{21}$
2Pyr-11,11 – $R^1, R^2 = C_{11}H_{23}$
2Pyr-12,12 – $R^1, R^2 = C_{12}H_{25}$
2Pyr-13,13 – $R^1, R^2 = C_{13}H_{27}$
2Pyr-14,14 – $R^1, R^2 = C_{14}H_{29}$
2Pyr-16,16 – $R^1, R^2 = C_{16}H_{33}$
2Pyr-18,18 – $R^1, R^2 = C_{18}H_{37}$ wherein each occurrence of Z is $Br^-$.

In one embodiment, the compound of formula IV is 2Pyr-11,11:

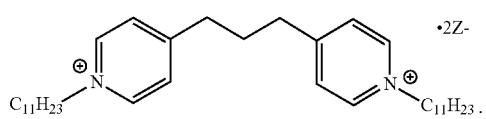

In one aspect, the compound of the invention is a polycationic (e.g., biscationic, triscationic, or the like) amphiphile. As used herein, the terms "amphiphile" and "amphiphilic" refer to a compound which has at least one hydrophilic moiety and at least one hydrophobic moiety. In one embodiment, the compound is monocationic. In one embodiment, the compound is a quaternary ammonium compound, or QAC, comprising at least one tetrasubstituted nitrogen atom. In some embodiments, the compound is comprised of two, three, four, five, six, seven, eight, nine, or ten tetrasubstituted nitrogen atoms. In one embodiment, the compound is comprised of three tetrasubstituted nitrogen atoms (triscationic). The amine may be protonated or it may not be protonated. In a non-limiting example, the compound comprises two cations and an amine, wherein the amine is protonated or unprotonated. In another non-limiting example, the compound comprises two cations and two amines, and the amines are independently protonated or unprotonated.

In some embodiments, a substituent may be null. As used herein, the term "null" refers to the group being absent. Accordingly, the number of substituents on the nitrogen to which the null group is attached and the number of corresponding counterions Z would each be reduced by one. In a non-limiting example, a compound of formula I where $R^1$ is null, and $R^1$ is no longer present in the compound and the nitrogen atom to which $R^1$ was attached becomes a trisubstituted nitrogen that does not have a positive charge. Accordingly, the number of the counterion Z in formula I is reduced from $3Z^-$ to $2Z^-$.

The counterion Z may be any ion which carries a charge(s) opposite to the charge on the compound. Non-limiting examples of counterions include halogen ions, mesylate ion, tosylate ion, triflate ion, carboxylate ions such as acetate, propionate, and stearate, and any ion that forms a pharmaceutically acceptable salt with the compound, such as pharmaceutically acceptable non-toxic acids, including inorganic acids, organic acids, solvates, hydrates, or clathrates. In one embodiment, the counterion Z is selected from the group consisting of a halogen ion, a mesylate ion, a tosylate ion, triflate ion, an acetate ion, a propionate ion, and a stearate ion. In another embodiment, the counterion Z is a halogen ion. In another embodiment, the counterion Z is a bromide ion.

Hybrid Polycationic Amphiphiles

In another aspect of the invention, the polycationic amphiphile is conjugated to or attached to a second compound or moiety. Any compound or moiety which may improve the biological properties of the polycationic amphiphile is contemplated for use within the invention. Non-limiting examples include QACs, antimicrobial peptides, sugars, iron siderophores, polymerizable moieties, solid surfaces such as glass, metal, paper or poly(alkyl ethers) such as polyethylene glycol (PEG) or polypropylene glycol (PPG), and other nucleophilic residues. In a non-limiting example, a first QAC can be attached to a second dicationic QAC to form a tetracationic QAC. The second dicationic QAC may be identical to the first dicationic QAC, resulting in a symmetrical tetracationic QAC, or it may be different, providing "chimeric" compounds with 4 cations, but dissimilar substituents. In one embodiment, the polycationic amphiphile is attached to a surface. In one embodiment, the surface is a solid surface. In one embodiment, the solid surface is a glass surface, a metal surface, a paper surface, or a poly(alkyl ether). In some embodiments, the polycationic amphiphile is attached to the additional compound or moiety via a bond. In other embodiment, the polycationic amphiphile is attached to the additional compound or moiety via a linker. The linker may be any suitable linker, as would be understood by one of ordinary skill the art. Examples of linkers include, but are not limited to, an alkyl group, a benzyl group, an aryl group, a heteroaryl group, a cycloalkyl group, an amide group, an ester, an amide, a sulfonamide, a carbamate, a carbonate, a sulfone, an ether, an oxime, a hydrazine, a urea, a thiourea, a phosphate, a poly(alkyl ether), or a heteroatom, wherein the group may be optionally substituted.

Antimicrobial Compositions

The compositions useful within the invention comprise at least one polycationic amphiphile. The compositions of the invention may be used in aqueous emulsions such as latexes, water-based paints and coatings, caulks and adhesives, tape joint compounds, mineral slurries, water-cooling systems, personal care products, soaps and detergents, disinfectants, cleaners, and sanitizers, pesticide products, oilfield water and water-based fluids used in oilfield applications including drilling muds, fracturing fluids, and hydrotest fluids, and the like. In one embodiment, the composition is an antimicrobial composition. In one embodiment, the composition is an antiseptic. In another embodiment, the composition is used for oil-pipeline cleaning. In another embodiment, the composition is used as an antifouling treatment for ships or other vessels used for transportation. In another embodiment, the composition is a solid-supported material.

The compositions useful within the invention may further comprise at least one additional antimicrobial agent. Non-limiting examples of the at least one additional antimicrobial agent are levofloxacin, doxycycline, neomycin, clindamycin, minocycline, gentamycin, rifampin, chlorhexidine, chloroxylenol, methylisothizolone, thymol, α-terpineol, cetylpyridinium chloride, hexachlorophene, triclosan, nitrofurantoin, erythromycin, nafcillin, cefazolin, imipenem, astreonam, gentamicin, sulfamethoxazole, vancomycin, ciprofloxacin, trimethoprim, rifampin, metronidazole, clindamycin, teicoplanin, mupirocin, azithromycin, clarithromycin, ofoxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linexolid, temafloxacin, tosufloxacin, clinafloxacin, sulbactam, clavulanic acid, amphotericin B, fluconazole, itraconazole, ketoconazole, nystatin, penicillins, cephalosporins, carbepenems, beta-lactams antibiotics, aminoglycosides, macrolides, lincosamides, glycopeptides, tetracylines, chloramphenicol, quinolones, fucidines, sulfonamides, trimethoprims, rifamycins, oxalines, streptogramins, lipopeptides, ketolides, polyenes, azoles, echinocandines, and any combination thereof.

In one embodiment, the polycationic amphiphile and the at least one additional antimicrobial agent act synergistically in preventing, reducing or disrupting microbial growth or formation of a biofilm on a surface. A synergistic effect may be calculated, for example, using suitable methods such as, for example, the Sigmoid-Emax equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The compositions useful within the invention may further include a microbial activity indicator, which is capable of indicating the presence of microorganisms on the at least one surface.

The composition useful within the invention may further comprise an acidic solution and glycerol. The acidic solution may comprise a short chain monocarboxylic acid (e.g., formic acid, acetic acid or propionic acid). The acidic solution may further comprise ortho-phosphoric acid. In one embodiment, the acidic solution further comprises a salt, such as potassium chloride.

In one preferred embodiment, the polycationic amphiphile is present in the composition in an amount sufficient to penetrate or disrupt a biofilm and allow access of the polycationic amphiphile, and/or the at least one additional antimicrobial agent to the biofilm-embedded microorganism, thereby facilitating the removal of at least a portion of the biofilm-embedded microorganisms from the at least one surface. In another preferred embodiment, the polycationic amphiphile is present in the composition in an amount sufficient to inhibit the growth or proliferation of microorganisms on the at least one surface, thereby facilitating the removal of at least a portion of the biofilm-embedded microorganisms from such surface. The polycationic amphiphile may constitute about 0.01% to about 100% (by weight) of the composition, about 0.1% to about 60% (by weight) of the composition, or about 0.5% to about 30% (by weight) of the composition.

The composition of the invention may further comprise a base material and a biofilm-penetrating agent. Non-limiting examples of suitable base materials include, but are not limited to, buffer solutions, phosphate buffered saline, saline, water, polyvinyl, polyethylene, polyurethane, polypropylene, polysiloxane (e.g., silicone elastomers and silicone adhesives), polycarboxylic acids, (e.g., polyacrylic acid, polymethacrylic acid, polymaleic acid, poly(maleic acid monoester), polyaspartic acid, polyglutamic acid, aginic acid or pectimic acid), polycarboxylic acid anhydrides (e.g., polymaleic anhydride, polymethacrylic anhydride or poly acrylic acid anhydride), polyamines, polyamine ions (e.g., polyethylene imine, polyvinylarnine, polylysine, poly-(dialkylamineoethyl methacrylate), poly(dialkylaminomethyl styrene) or poly-(vinylpyridine)), poly ammonium ions (e.g., poly-(2-methacryloxyethyl trialkyl ammonium ion), poly-(vinylbenzyl trialkyl ammonium ions), poly-(N-alkylypyridinium ion) or poly(dialkyloctamethylene ammonium ion) and polysulfonates (e.g. poly-(vinylsulfonate) or poly-(styrene sulfonate)), collodion, nylon, rubber, plastic, polyesters, Gortex® (polytetrafluoroethylene), Dacron® (polyethylene tetraphthalate), Teflon® polytetrafluoroethylene), latex and derivatives thereof, elastomers and Dacron® sealed with gelatin, collagen or albumin, cyanoacrylates, methacrylates, papers with porous barrier films, adhesives (e.g., hot melt adhesives, solvent based adhesives, and adhesive hydrogels), fabrics, and crosslinked and non-crosslinked hydrogels, and any other polymeric materials that facilitate dispersion of the biofilm-penetrating agent and adhesion of the biofilm-penetrating coating to the at least one surface. Linear copolymers, cross-linked copolymers, graft polymers, and block polymers, containing monomers as constituents of the above exemplified polymers may also be used.

In the case of internal or external use of the biofilm-penetrating composition on humans or animals, the polycationic amphiphile and the base material should be biocompatible with the human beings or animals on which body surface the composition is applied.

The invention further includes a coated surface, which includes a composition comprising at least one polycationic amphiphile applied to the surface. In one embodiment, the composition comprises at least one polymer of the invention. In one embodiment, the surface is coated with a compound or composition of the invention. In one embodiment, the surface is selected from the group consisting of a glass surface, a metal surface, a paper surface, or a polymer surface. In one embodiment, a surface may be functionalized and coated with multicationic QACs. Such surfaces are useful in medical settings (e.g., antimicrobial surfaces) and antiseptic-coated indwelling devices (e.g., antimicrobial plastics, stents, joint replacements, and the like). The invention further includes a film or coating comprising at least one polycationic amphiphile of the invention. The composition may be applied to the desired surface in any suitable manner, as described herein or as known to those skilled in the art.

In one embodiment, a septum, or adhesive layer, is made of a breathable material that has small enough porosity to allow moisture to pass, but functions as a barrier to microorganisms thereby facilitating a lower incidence of microorganism colonization and resulting contamination or infection. The adhesive layer may also include a layer of gauze to facilitate a lower incidence of microorganism colonization and resulting contamination or infection.

Medical Devices

The invention contemplates applying to or coating medical devices with the compositions useful within the invention. Non-limiting examples of medical devices include disposable or permanent catheters, (e.g., central venous catheters, dialysis catheters, long-term tunneled central venous catheters, short-term central venous catheters, arterial catheters, peripherally inserted central catheters, peripheral venous catheters, pulmonary artery Swan-Ganz catheters, urinary catheters, and peritoneal catheters, drainage catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings (e.g., intravenous tubes, breathing tubes, dental water lines, dental drain tubes, and feeding tubes), fabrics, paper, indicator strips (e.g., paper indicator strips or plastic indicator strips), adhesives (e.g., hydrogel adhesives, hot-melt adhesives, or solvent-based adhesives), bandages, orthopedic implants, and any other device used in the medical field.

Medical devices also include any device that may be inserted or implanted into a human being or other animal, or placed at the insertion or implantation site such as the skin near the insertion or implantation site, and that include at least one surface which is susceptible to colonization by microorganisms and/or biofilm-embedded microorganisms. Also contemplated within the invention is any other surface that may be desired or necessary to prevent microorganisms and/or biofilm-embedded microorganisms from growing or proliferating on at least one surface of the medical device, or to remove or clean microorganisms and/or biofilm-embedded microorganisms from the at least one surface of the medical device, such as the surfaces of equipment in operating rooms, emergency rooms, hospital rooms, clinics, and bathrooms. In one specific embodiment, the composition is integrated into an adhesive, such as tape, thereby providing an adhesive that may prevent or reduce growth or proliferation of microorganisms and/or biofilm embedded-microorganisms on at least one surface of the adhesive.

Implantable medical devices include orthopedic implants that may be inspected for contamination or infection by microorganisms and/or biofilm-embedded microorganisms using endoscopy. Insertable medical devices include catheters and shunts that can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex® (polytetrafluoroethylene), Dacron® (polyethylene tetraphthalate), Teflon® (polytetrafluoroethylene), latex, elastomers and Dacron® sealed with gelatin, collagen or albumin, and derivatives or combinations thereof. The medical devices include at least one surface for applying the biofilm-penetrating composition. In one embodiment, the biofilm-penetrating composition is applied to the entire medical device.

Methods

The invention includes a method of preventing or reducing the growth or proliferation of microorganisms and/or biofilm-embedded microorganisms on at least one surface. The method includes the steps of: providing at least one surface; providing a composition comprising a polycationic amphiphile, and applying the composition to the at least one surface in an amount sufficient to prevent or reduce the growth or proliferation of microorganisms or biofilm-embedded microorganisms on the at least one surface. In one embodiment, the surface is a subject's body. In another embodiment, the surface is at least one surface of a medical device. In another embodiment, the surface is a solid surface. In another embodiment, the surface is selected from the group consisting of a glass surface, a metal surface, a paper surface, or a polymer surface.

In one embodiment, the composition further comprises a base material. In another embodiment, preparation of the composition comprises contacting the polycationic amphiphile and the base material at room temperature and mixing the resulting mixture for a time sufficient to evenly disperse the polycationic amphiphile in the composition prior to contacting the surface with the composition. The concentration of polycationic amphiphile in the composition may be varied as desired or necessary to decrease the amount of time the composition is in contact with the surface. These variations in concentration of polycationic amphiphile are easily determined by persons skilled in the art. In another embodiment, at least one surface is contacted with the composition under conditions wherein the composition covers at least part of the surface.

In one embodiment, the composition further comprises an organic solvent or an alkalinizing agent, either of which enhances the reactivity of the surface of the medical device with the composition. In another embodiment, the organic solvent and/or alkalinizing agent facilitates adhesion of the composition to the at least one surface.

The invention also includes a method of removing at least a portion of or reducing the number of microorganisms and/or biofilm embedded microorganisms attached to at least one surface. The method comprises the steps of: providing at least one surface, wherein the at least one surface comprises microorganisms and/or biofilm-embedded microorganisms attached thereto; and contacting the least one surface with a composition comprising at least one polycationic amphiphile, whereby at least a portion of the microorganisms and/or biofilm embedded microorganisms are removed from the at least one surface or the number of microorganisms and/or biofilm embedded microorganisms attached to the at least one surface is reduced. The contact between the at least one surface and the composition should last for a period of time sufficient to remove at least a portion of the microorganisms and/or biofilm-embedded microorganisms from at least one surface or reduce the number of microorganisms and/or biofilm embedded microorganisms attached to the at least one surface. In one embodiment, the surface is a subject's body. In another embodiment, the surface is at least one surface of a medical device. In another embodiment, the surface is a solid surface. In another embodiment, the surface is selected from the group consisting of a glass surface, a metal surface, a paper surface, or a polymer surface.

Pharmaceutical Compositions and Formulations

The invention also encompasses the use of pharmaceutical compositions comprising a polycationic amphiphile, for inhibiting or disrupting microorganism growth or the formation of biofilms on a surface of a subject's body. Such a pharmaceutical composition may consist of the polycationic amphiphile in a form suitable for administration to a subject. The polycationic amphiphile may be present in the pharmaceutical composition in the form of a physiologically acceptable salt, such as in combination with a physiologically acceptable cation, as is well known in the art.

In an embodiment, the pharmaceutical compositions useful for practicing the method of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, topical, transdermal, ophthalmic, intrathecal or another route of administration. The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention or reduction of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Formulations may be employed in admixtures with conventional excipients. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; antiseptics; antiviral agents; anticoagulants; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent which inhibit the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition which may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as *arachis*, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as *Arachis*, olive, sesame, or coconut oil, fractionated vegetable oils, and mineral oils such as liquid paraffin.

Administration/Dosing

The regimen of administration may affect what constitutes an effective amount. The therapeutic formulations may be administered to the patient either prior to or after the onset of pathogenic colonization, biofilm formation, and/or infection in a patient. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to prevent, reduce or disrupt pathogenic colonization, biofilm formation, and/or infection in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. One of ordinary skill in the art would be able to study the relevant factors and make the determination regarding the effective amount of the therapeutic compound without undue experimentation.

The compound can be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of breathing control disorders in a patient.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

In one embodiment, the present invention is directed to a packaged pharmaceutical composition comprising a container holding a therapeutically effective amount of a compound of the invention, alone or in combination with a second pharmaceutical agent; and instructions for using the compound to prevent or reduce the growth or proliferation of microorganisms or biofilm-embedded microorganisms on at least one surface of a medical device or a subject's body.

Routes of Administration

Routes of administration of any of the compositions of the invention include rectal, transdermal, transmucosal (e.g., sublingual, lingual, (trans)buccal, (trans)urethral, vaginal (e.g., trans- and perivaginally), (trans)rectal, intravesical, and topical administration.

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, gels, lotions, oil-in-water or water-in-oil emulsions such as creams, ointments or pastes, and solutions or suspensions. Topically administrable formulations may, for example, comprise from about 1% to about 10% (w/v) active ingredient in a solvent, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide (DMSO), and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (for example, see Constanza, U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In another embodiment, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.001% to about 1% of the composition. Such compounds may be synthetically- or naturally derived.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Figure 2:
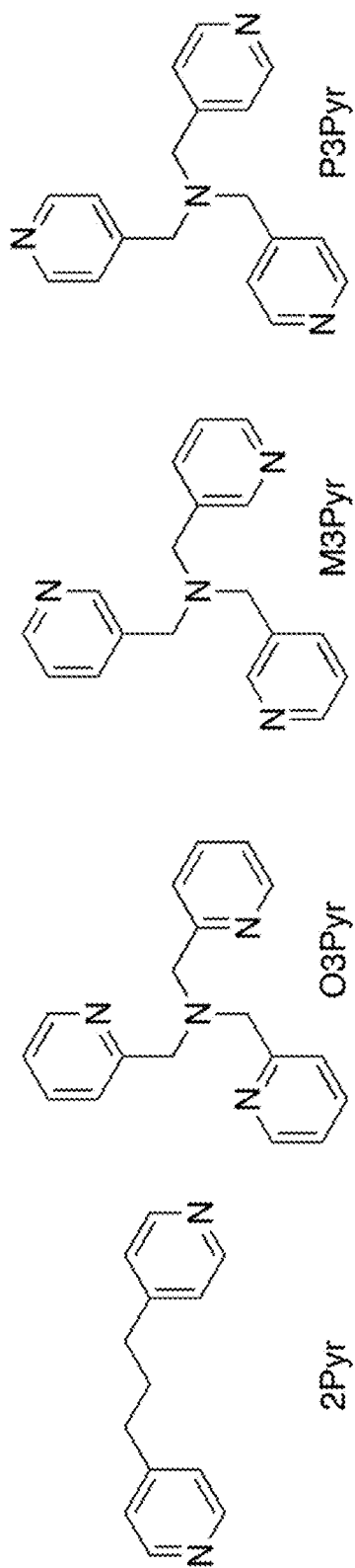
FIG. 2 is an image depicting multipyridine core structures for the construction of pyridinium multiQACs.

Example 1: The Development of Next Generation Pyridinium-Based multiQAC Antiseptics A series of 18 bis- and tris-pyridinium amphiphiles were prepared and tested for both antimicrobial activity and lytic capability, in comparison to the commercially available pyridinium antiseptic cetylpyridinium chloride (CPC). Specifically, the antimicrobial activity of a variety of structures bearing two or three pyridinium groups, starting with core structures that were designated as 2Pyr and 3Pyr, were examined (FIG. 2). While 2Pyr derivatives were known to be alkylated to form amphiphiles of various utility, ranging from host-guest chemistry (Yang et al., 2016, Chem. Eng. J. 285:27-38) to DNA interaction (Barbero et al., 2015, chemPluschem 80:952-962), nothing conclusive was known about their antimicrobial activity (U.S. Pat. Nos. 3,786,058, 3,875,174). Alkylation of tris-pyridine core structures such as the commercially available O3Pyr, or its readily-synthesized isomers P3Pyr (Oh et al., 2007, Bull. Korean Chem. Soc. 28:2193-2194) and M3Pyr (Fromherz and Spiegelberg, 1948, Helv. Physiol. Pharmacol. Acta 6:42-54), showed no literature precedents, and thus served as a starting point. Assessments were made against Gram-positive and Gram-negative bacteria, including two methicillin-resistant *Staphylococcus aureus* (MRSA) strains. While 2Pyr-11,11 was identified as one of the most potent antimicrobial QACs reported to date, boasting nanomolar inhibition against 5 of 6 bacteria tested, no significant improvement in bioactivity of tris-pyridinium amphiphiles over their bis-pyridinium counterparts was observed. However, the multiQACs presented herein did display significant advantages over the monocationic CPC; while comparable red blood cell lysis was observed, superior activity against both Gram-negative bacteria and resistant *S. aureus* strains led to the discovery of four pyridinium-based multiQACs with advantageous therapeutic indices.

Results

Figure 3:
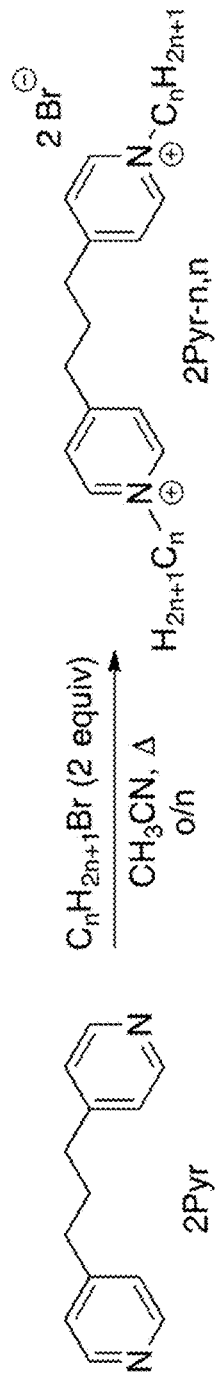
FIG. 3 is an image depicting the preparation of the 2Pyr-n,n series of amphiphiles.

The synthetic preparation of a variety of bis- and tris-pyridinium compounds in short synthetic sequences was performed, starting with the commercially available 1,3-di-(4-pyridyl)propane (FIG. 3), eight bispyridinium compounds of varying chain length were prepared in high yields, after exposure to the corresponding alkyl bromides (in excess) overnight in acetonitrile at reflux. The resulting amphiphiles were purified via precipitation and subsequent recrystallization or trituration. Complete experimental details as well as compound characterization for all prepared compounds are presented in this invention.

Figure 4:
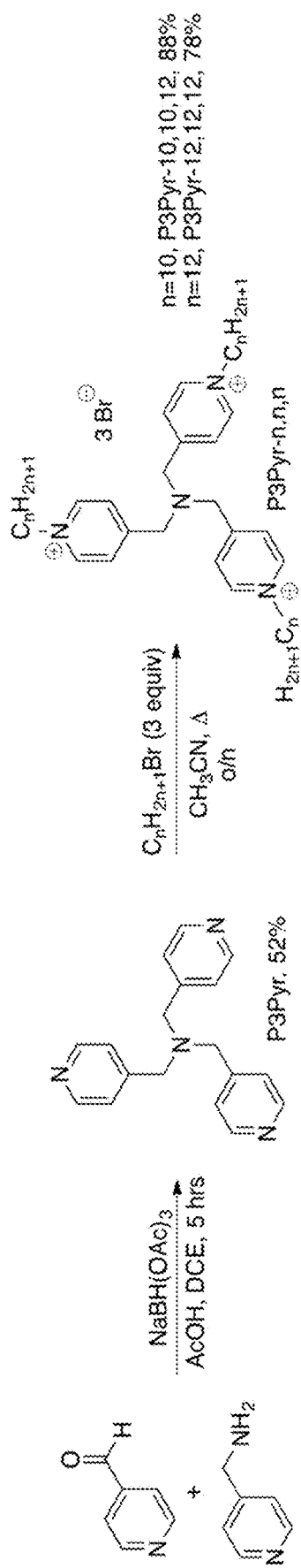
FIG. 4 is an image depicting the preparation of the P3Pyr-n,n series of amphiphiles.
Figure 5:
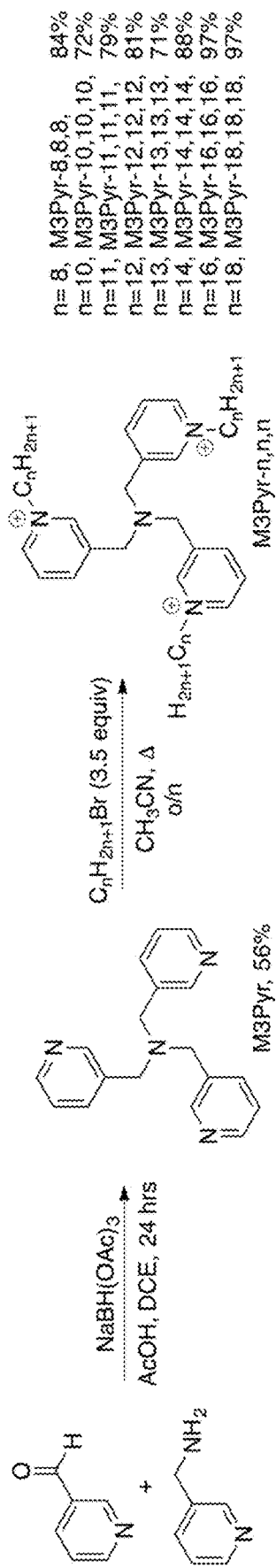
FIG. 5 is an image depicting the preparation of the M3Pyr-n,n series of amphiphiles.

For the tris-pyridine system, it was initially attempted to alkylate the commercially available O3Pyr, which led to no reaction under a number of $S_N2$-type reaction conditions, presumably due to steric hindrance next to the nucleophilic pyridine nitrogen. The preparation of the "para" isomer via a precedented reductive amination shown in FIG. 4 (52%) was then carried out (Oh et al., 2007, Korean Chem. Soc, 28: 2193-2194, Abdel-Magid et al., 1996, J. Org. Chem, 61: 3849-3862). This, however, led to poor reproducibility in the subsequent alkylation; P3Pyr-10,10,10 and P3Pyr-12,12,12 were prepared in good yield but showed poor stability. Attempts to prepare homologs led to variable yields and unacceptable purity. While not wishing to be bound by any particular theory it was hypothesized that this could have resulted from a fragmentation event driven by the central nitrogen, which might be circumvented by a change in the electronic distribution of the QAC. It was demonstrated that the "meta" tris-pyridine isomer M3Pyr was readily prepared via reductive amination (56%), (Fromherz, et al., 1948, Physiol. Pharmacol. Acta., 6: 42-54) and alkylation thereof was facile and produced shelf-stable compounds titled M3Pyr-n,n,n (FIG. 5). These amphiphiles were prepared in 71-97% yields, again after recrystallization or trituration. With 18 novel multi-pyridinium compounds in hand, varying in both alkyl chain length and number of pyridinium residues, both antimicrobial activity and toxicity of the compounds were examined, using red blood cell lysis as a model; CPC served as a comparison. These assessments followed standard protocols (Minbiole et al., 2016, Tetrahedron, 72: 3559-3566, Forman et al., 2016, ChemMedChem, 11: 1401-1405, Forman et al., 2016, ChemMedChem, 11: 958-962, Mitchell et al., 2015, ChemBioChem, 16: 2299-2303, Jennings et al., 2015, ACS Inf. Dis, 1: 304-308, Paniak et al., 2014, Bioorg. Med. Chem. Lett, 24: 5824-5828, Ator et al., 2014, Bioorg. Med. Chem. Lett, 24: 3706-3709, Jennings et al., 2014, ChemBioChem, 15: 2211-2215, Black et al., 2014, Bioorg. Med. Chem. Lett, 24, 99-102, Grenier et al., 2012, Bioorg. Med. Chem. Left, 22: 4055-4058). The complete set of MIC values against six bacteria [*Staphylococcus aureus* (SA), *Enterococcus faecalis* (EF), *Escherichia coli* (EC), and *Pseudomonas aeruginosa* (PA), community-acquired methicillin-resistant SA (CA-MRSA), hospital-acquired methicillin-resistant SA (HA-MRSA)], along with red blood cell lysis (presented as $lysis_{20}$, the highest concentration at which <20% of RBCs are lysed), are presented in Table 1.

TABLE 1

Antimicrobial activity and red blood cell lysis data for amphiphiles, presented in μM.

| Compound | MIC, μM | | | | | | Lysis$_{20}$ (μM) |
| --- | --- | --- | --- | --- | --- | --- | --- |
| | S. aureus | E. faecalis | E. coli | P. aeruginosa | CA-MRSA | HA-MRSA | |
| CPC | 0.5 | 1 | 8 | 63 | 16 | 1 | 8 |
| 2Pyr | >250 | >250 | >250 | >250 | >250 | >250 | >250 |
| 2Pyr-8,8 | 8 | 63 | 32 | >250 | 16 | 63 | 125 |
| 2Pyr-10,10 | 0.5 | 1 | 0.5 | 16 | 0.25 | 1 | 16 |
| 2Pyr-11,11 | 0.5 | 0.25 | 0.5 | 2 | 0.25 | 0.5 | 8 |
| 2Pyr-12,12 | 0.5 | 0.5 | 1 | 4 | 0.25 | 0.5 | 4 |
| 2Pyr-13,13 | 0.5 | 0.5 | 1 | 8 | 0.25 | 0.5 | 16 |
| 2Pyr-14,14 | 8 | 1 | 4 | 250 | 2 | 2 | 63 |
| 2Pyr-16,16 | 4 | 8 | 63 | >250 | 4 | 8 | 63 |
| 2Pyr-18,18 | 8 | 8 | >250 | >250 | 4 | 16 | 32 |
| M3Pyr | 250 | >250 | >250 | >250 | 250 | 250 | >250 |
| P3Pyr | >250 | >250 | >250 | >250 | >250 | >250 | 125 |
| M3Pyr-8,8,8 | 2 | 8 | 8 | 32 | 1 | 2 | >250 |
| M3Pyr-10,10,10 | 0.5 | 1 | 1 | 2 | 0.5 | 0.5 | 4 |
| P3Pyr-10,10,10 | 0.5 | 1 | 1 | 2 | 0.5 | 0.5 | 4 |
| M3Pyr-11,11,11 | 0.5 | 1 | 1 | 4 | 0.5 | 0.5 | 4 |
| M3Pyr-12,12,12 | 1 | 1 | 1 | 8 | 0.5 | 1 | 4 |
| P3Pyr-12,12,12 | 2 | 2 | 2 | 8 | 1 | 2 | 8 |
| M3Pyr-13,13,13 | 1 | 1 | 2 | 8 | 0.25 | 0.5 | 2 |
| M3Pyr-14,14,14 | 2 | 2 | 4 | 32 | 1 | 1 | 4 |
| M3Pyr-16,16,16 | 2 | 8 | 125 | ≥250 | 4 | 2 | 4 |
| M3Pyr-18,18,18 | 8 | 32 | 63 | >250 | 4 | 4 | 8 |

The antimicrobial data from 19 pyridinium amphiphiles plus three core multi-amines was examined. First, the core structures showed essentially no activity. Next, correlation of antimicrobial activity to the chain length of the non-polar side chains of the amphiphiles was observed. Whereas CPC holds a single 16-carbon chain, potent activity in the 2-Pyr series was observed for the 11-carbon chain (2Pyr-11,11), and one carbon shorter was observed to provide potent activity in the 3Pyr series (i.e., M3Pyr-10,10,10 and P3Pyr-10,10,10). Further, it was noted that there was no significant difference in bioactivity between the isomeric M3Pyr and P3Pyr series, the latter of which is bolded in Table 1.

The correlation of the number of pyridinium groups to bioactivity was somewhat surprising; against Gram-positive bacteria (SA and EF), strongly bioactive compounds from all three groups were comparable in activity (MIC ~0.25-1 μM). However, the monocationic CPC showed diminished activity against Gram-negative bacteria (EC and PA) as well as against the CA-MRSA strain. This latter observation was significant; there was a 32-fold increase in MIC when comparing the ability of CPC to inhibit CA-MRSA as compared to a non-resistant SA strain, which is a hallmark of bacterial resistance. Conversely, only one example of antibacterial resistance (8-fold increase) in the smallest multiQAC, 2Pyr-8,8 was observed. For chain lengths between 10-13 carbons, bioactivity was uniformly strong for both the 2Pyr and 3Pyr systems.

Hemolysis activity, measured as lysis$_{20}$, roughly correlated to chain length across all compounds in the 2Pyr series, with a lowest value of 4 μM in the case of 2Pyr-12,12. Pleasingly, lysis$_{20}$ values were approximately 8 to 16 times the MIC against Gram-positive species, though for the M3Pyr series, the therapeutic index (ratio of antimicrobial activity to RBC lysis) was diminished. A therapeutic window was observed for two bis- and two trisQACs—for these compounds, the lysis$_{20}$ exceeded the highest MIC tested; this was not the case for CPC, whose lysis$_{20}$ value (8 μM) was smaller than the MIC against MRSA or PA (16 and 63 μM, respectively).

The observed increase in RBC lysis for the third pyridinium residue is noteworthy as it has been previously postulated that an increase in cationic charge may improve the therapeutic index, owing to the differential cell membrane composition of eukaryotic versus prokaryotic cells. While this appears to not be the case within the 3Pyr series, it is noted that lysis$_{20}$ is a rather strict assessment of toxicity. Although not wishing to be bound to any particular theory, these results may hint at the importance of the three-dimensional projection of the side chains in tuning selectivity between bacterial and mammalian cell membranes.

In summary, this study investigated the antimicrobial activity of related families of pyridinium amphiphiles. The multiQACs presented herein show significant advantages over the monocationic CPC; activity against both Gram-negative bacteria and resistant MRSA strains were up to 64× better for the multiQACs. Although not wishing to be bound to any particular theory, this may be a result of subtle structural intricacies born by each QAC, and if true, would permit the design of improved multiQACs. In light of the therapeutic window, it is clear that pyridinium-based multiQACs are candidates to be used as antimicrobial agents.

Synthesis of Compounds

Reagents and solvents were used from Sigma-Aldrich, Acros, TCI America, and Alfa Aesar without further purification. All reactions were carried out under ambient atmosphere with reagent grade solvents and magnetic stirring. All yields refer to spectroscopically pure compounds. $^1$H NMR spectra were measured with a 300 MHz Varian spectrophotometer, and chemical shifts were reported on a δ-scale (ppm) downfield from TMS. Coupling constants were calculated in hertz. $^{13}$C NMR spectra were obtained at 75 MHz, and results were reported on a δ-scale (ppm). Chloroform-d (CDCl$_3$) was the solvent used for all NMR samples with an internal reference of 7.26 ppm.

Preparation of 2Pyr-8,8

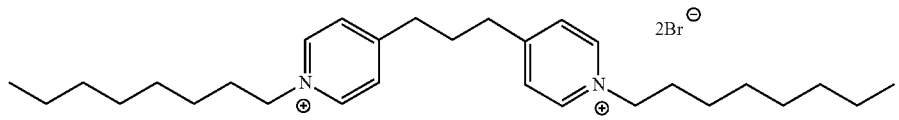 [SMILES: CCCCCCCC[n+]1ccc(CCCc2cc[n+](CCCCCCCC)cc2)cc1]

To a solution of 1,3-di-(4-pyridyl)propane (0.508 g, 2.56 mmol) in acetonitrile (1 mL) was added 1-bromooctane (0.989 g, 5.12 mmol). The resulting clear solution was heated at reflux with stirring overnight, which resulted in the precipitation of a beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-8,8 (1.36 g, 91%) as a sticky red/orange solid; $^1$H NMR (300 MHz, CDCl$_3$) δ 8.97 (d, J=6.0 Hz, 4H), 8.11 (d, J=6.0 Hz, 4H), 4.71-4.66 (m, 4H), 3.05-3.00 (m, 4H), 2.24-2.13 (m, 2H), 1.91-1.89 (m, 4H), 1.25-1.16 (m, 24H), 0.81-0.76 (m, 6H); $^{13}$C NMR (75 MHz, CDCl$_3$) δ 161.7, 144.1, 128.8, 61.9, 35.4, 31.6, 28.9, 26.1, 22.4, 14.1; mass spectrum m/z: 212.3 ([M]$^{2+}$; calculated for [C$_{29}$H$_{48}$N$_2$]$^{2+}$: 212.2).

Preparation of 2Pyr-10,10

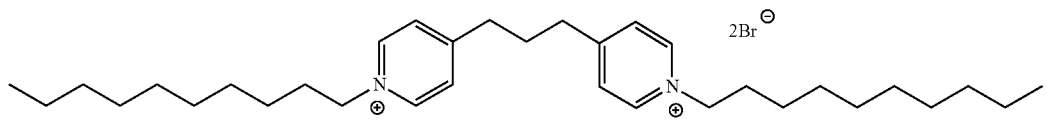 [SMILES: CCCCCCCCCC[n+]1ccc(CCCc2cc[n+](CCCCCCCCCC)cc2)cc1]

To a solution of 1,3-di-(4-pyridyl)propane (0.508 g, 2.56 mmol) in acetonitrile (1 mL) was added 1-bromodecane (1.13 g, 5.11 mmol). The resulting clear solution was heated at reflux with stirring overnight, which resulted in the precipitation of a light beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-10,10 (1.42 g, 79%) as a light brown powder; mp: 71.2-74.5° C.; $^1$H NMR (300 MHz, CDCl$_3$) δ 8.89 (d, J=6.0 Hz, 4H), 8.05 (d, J=6.0 Hz, 4H), 4.66-4.61 (m, 4H), 3.05-3.00 (m, 4H), 2.31-2.26 (m, 2H), 1.91-1.87 (m, 4H), 1.26-1.17 (m, 28H), 0.82-0.78 (m, 6H); $^{13}$C NMR (75 MHz, CDCl$_3$) δ 161.8, 144.1, 128.8, 61.4, 34.7, 31.7, 31.5, 29.4, 29.3, 29.2, 28.9, 26.1, 22.5, 13.9; mass spectrum m/z: 240.2 ([M]$^{2+}$; calculated for [C$_{33}$H$_{56}$N$_2$]$^{2+}$: 240.2).

Preparation of 2Pyr-11,11

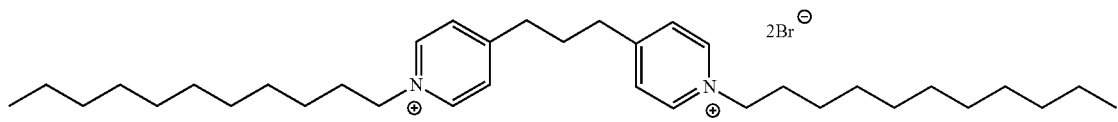 [SMILES: CCCCCCCCCCC[n+]1ccc(CCCc2cc[n+](CCCCCCCCCCC)cc2)cc1]

To a solution of 1,3-di-(4-pyridyl)propane (0.402 g, 2.03 mmol) in acetonitrile (1 mL) was added 1-bromoundecane (0.955 g, 4.06 mmol). The resulting clear solution was heated at reflux with stirring overnight, which resulted in the precipitation of a light beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-11,11 (1.27 g, 93%) as a copper-colored powder; mp: 79.5-84.4° C.; $^1$H NMR (300 MHz, CDCl$_3$) δ 9.04 (d, J=6.0 Hz, 4H), 8.17 (d, J=6.0 Hz, 4H), 4.77-4.73 (m, 4H), 3.10-3.05 (m, 4H), 2.27-2.22 (m, 2H), 1.98-1.94 (m, 4H), 1.29-1.21 (m, 32H), 0.87-0.82 (m, 6H); $^{13}$C NMR (75 MHz, CDCl$_3$) δ 161.8, 144.1, 128.8, 61.4, 34.7, 31.8, 31.6, 29.5, 29.4, 29.3, 29.2, 29.0, 26.1, 22.6, 13.9; mass spectrum m/z: 254.4 ([M]$^{2+}$; calculated for [C$_{35}$H$_{60}$N$_2$]$^{2+}$: 254.2).

Preparation of 2Pyr-12,12

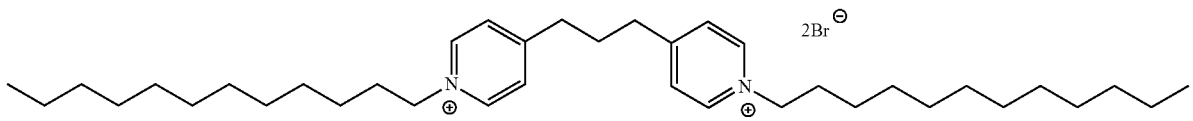 [SMILES: CCCCCCCCCCCC[n+]1ccc(CCCc2cc[n+](CCCCCCCCCCCC)cc2)cc1]

To a solution of 1,3-di-(4-pyridyl)propane (0.395 g, 1.99 mmol) in acetonitrile (1 mL) was added 1-bromododecane (0.992 g, 3.98 mmol). The resulting clear solution was heated at reflux with stirring overnight, which resulted in the precipitation of a beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-12,12 (1.72 g, 88%) as a light beige powder; mp: 77.3-84.2° C.; $^1$H NMR (300 MHz, CDCl$_3$) δ 9.05 (d, J=6.0 Hz, 4H), 8.19 (d, J=6.0 Hz, 4H), 4.78-4.73 (m, 4H), 3.13-3.08 (m, 4H), 2.32-2.27 (m, 2H), 1.97-1.91 (m, 4H), 1.31-1.23 (m, 36H), 0.88-0.84 (m, 6H); $^{13}$C NMR (75 MHz, CDCl$_3$) δ 161.9, 144.0, 128.8, 61.3, 34.8, 31.8, 29.5, 29.4, 29.3, 28.9, 22.6, 14.1; mass spectrum m/z: 268.4 ([M]$^{2+}$; calculated for [C$_{37}$H$_{64}$N$_2$]$^{2+}$: 268.3).

Preparation of 2Pyr-13,13

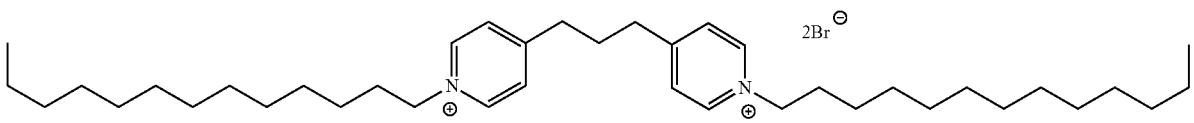 [SMILES: CCCCCCCCCCCCC[n+]1ccc(CCCc2cc[n+](CCCCCCCCCCCCC)cc2)cc1]

To a solution of 1,3-di-(4-pyridyl)propane (0.101 g, 0.509 mmol) in acetonitrile (1 mL) was added 1-bromotridecane (0.269 g, 1.02 mmol). The resulting clear solution was heated at reflux with stirring overnight, which resulted in the precipitation of a dark beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-13,13 (0.342 g, 93%) as an orange powder; mp: 83.7-87.8° C.; $^1$H NMR (300 MHz, CDCl$_3$) δ 8.94 (d, J=6.0 Hz, 4H), 8.10 (d, J=6.0 Hz, 4H), 4.69-4.64 (m, 4H), 3.05-2.99 (m, 4H), 2.26-2.21 (m, 2H), 1.86-1.88 (m, 4H), 1.25-1.17 (m, 44H), 0.83-0.78 (m, 6H); $^{13}$C NMR (75 MHz, CDCl$_3$) δ 161.7, 144.1, 128.8, 61.5, 34.7, 31.8, 31.5, 29.6, 29.5, 29.4, 29.3, 29.0, 28.9, 26.1, 22.6, 14.0; mass spectrum m/z: 282.2 ([M]$^{2+}$; calculated for [C$_{39}$H$_{68}$N$_2$]$^{2+}$: 282.3).

Preparation of 2Pyr-14,14

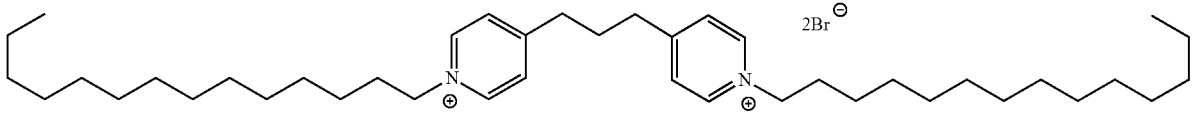 [SMILES: CCCCCCCCCCCCCC[n+]1ccc(CCCc2cc[n+](CCCCCCCCCCCCCC)cc2)cc1]

To a solution of 1,3-di-(4-pyridyl)propane (0.497 g, 2.51 mmol) in acetonitrile (1 mL) was added 1-bromotetradecane (1.39 g, 5.01 mmol). The resulting clear solution was heated at reflux with stirring overnight, which resulted in the precipitation of beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-14,14 (1.81 g, 96%) as a light beige powder; mp: 85.4-93.3° C.; $^1$H NMR (300 MHz, CDCl$_3$) δ 8.97 (d, J=6.0 Hz, 4H), 8.11 (d, J=6.0 Hz, 4H), 4.69-4.65 (m, 4H), 3.06-3.02 (m, 4H), 2.23-2.25 (m, 2H), 1.91-1.73 (m, 4H), 1.25-1.17 (m, 48H), 0.83-0.78 (m, 6H); $^{13}$C NMR (75 MHz, CDCl$_3$) δ 161.6, 144.1, 128.8, 110.0, 61.5, 34.8, 31.9, 31.5, 29.6, 29.6, 29.5, 29.4, 29.3, 28.9, 26.1, 22.6, 14.0; mass spectrum m/z: 296.6 ([M]$^{2+}$; calculated for [C$_{41}$H$_{72}$N$_2$]$^{2+}$: 296.3).

Preparation of 2Pyr-16,16

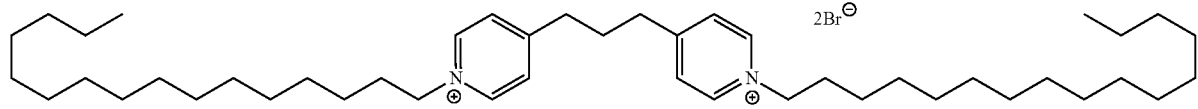 [SMILES: CCCCCCCCCCCCCCCC[n+]1ccc(CCCc2cc[n+](CCCCCCCCCCCCCCCC)cc2)cc1]

To a solution of 1,3-di-(4-pyridyl)propane (0.513 g, 2.58 mmol) in acetonitrile (1 mL) was added 1-bromohexadecane (1.58 g, 5.17 mmol). The resulting clear solution was heated at reflux with stirring overnight, which resulted in the precipitation of a beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-16,16 (1.98 g, 95%) as a light beige powder; mp: 89.8-96.7° C.; $^1$H NMR (300 MHz, CDCl$_3$) δ 9.04 (d, J=6.0 Hz, 4H), 8.18 (d, J=6.0 Hz, 4H), 4.77-4.73 (m, 4H), 3.13-3.08 (m, 4H), 2.35-2.25 (m, 2H), 1.97-1.93 (m, 4H), 1.31-1.11 (m, 48H), 0.88-0.84 (m, 6H); $^{13}$C NMR (75 MHz, CDCl$_3$) δ 161.7, 144.1, 128.8, 61.6, 34.4, 29.7, 29.6, 29.3, 22.6, 14.9; mass spectrum m/z: 324.5 ([M]$^{2+}$; calculated for [C$_{45}$H$_{80}$N$_2$]$^{2+}$: 324.3).

Preparation of 2Pyr-18,18

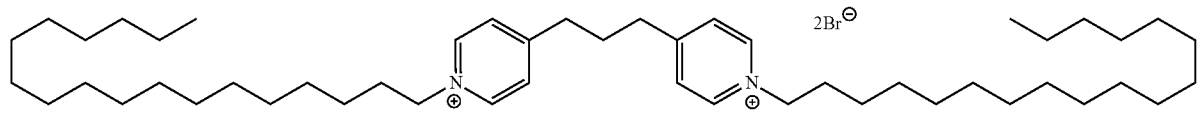 [SMILES: CCCCCCCCCCCCCCCCCC[n+]1ccc(CCCc2cc[n+](CCCCCCCCCCCCCCCCCC)cc2)cc1]

To a solution of 1,3-di-(4-pyridyl)propane (0.501 g, 2.53 mmol) in acetonitrile (1 mL) was added 1-bromooctadecane (1.68 g, 5.06 mmol). The resulting clear solution was heated at reflux with stirring overnight, which resulted in the precipitation of a light beige solid with a darker top layer. The reaction flask was cooled to room temperature, and cold acetone (~7 mL) was added. The resulting crude mixture was filtered with a Büchner funnel, and rinsed with cold acetone (~10 mL). The resulting solid beige product was triturated with hot acetone:hexanes (~15 mL, 1:1), and then washed with cold acetone:hexanes (~40 mL, 1:1), resulting in 2Pyr-18,18 (2.13 g, 97%) as a light beige powder; mp: 93.6-98.1° C.; $^1$H NMR (300 MHz, CDCl$_3$) δ 9.04 (d, J=6.0 Hz, 4H), 8.18 (d, J=6.0 Hz, 4H), 4.77-4.2 (m, 4H), 3.13-3.08 (m, 4H), 2.33-2.27 (m, 2H), 2.00-1.90 (m, 4H), 1.31-1.17 (m, 48H), 0.89-0.85 (m, 6H); $^{13}$C NMR (75 MHz, CDCl$_3$) δ 161.7, 144.1, 128.8, 61.5, 33.2, 31.8, 31.5, 29.7, 29.6, 29.5, 29.4, 29.3, 28.9, 26.1, 22.6, 15.1; mass spectrum m/z: 352.5 ([M]$^{2+}$; calculated for [C$_{49}$H$_{88}$N$_2$]$^{2+}$: 352.4).

Preparation of M3Pyr

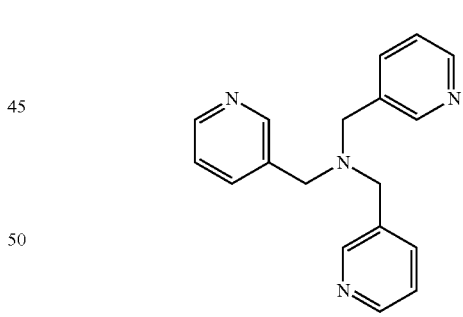

To a solution of 3-(aminomethyl)pyridine (1.42 g, 13.7 mmol) in acetic acid (5 mL) and 1,2-dichloroethane (20 mL) in an ice bath, was added sodium triacetoxyborohydride (7.29 g, 34.4 mmol) followed by 3-pyridinecarboxaldehyde (2.95 g, 27.5 mmol) with stirring. The resulting yellow mixture was allowed to warm to room temperature and stirred for 24 hours. The crude mixture was concentrated in vacuo, diluted with dichloromethane (30 mL), and washed twice with aqueous sodium bicarbonate (20 mL, saturated). The resulting organic solution was then washed with sodium hydroxide (10 mL, 1M) 3 times, resulting in M3Pyr (2.35 g, 56%) as a white crystalline solid; mp: 74.3-80.7° C.; $^1$H NMR (300 MHz, CDCl$_3$) δ 8.58 (d, J=1.8 Hz, 3H), 8.51 (dd, 1.5 Hz, 3H), 7.68 (dt, J=6.3, 1.8 Hz, 3H), 7.27 (dd, 4.8 Hz, 3H), 3.58 (s, 6H); $^{13}$C NMR (75 MHz, CDCl$_3$) δ 150.1, 148.9, 136.3, 133.9, 123.5, 55.4; mass spectrum m/z: 291.0 ([M+H$^+$]$^+$; calculated for [C$_{18}$H$_{19}$N$_4$]: 291.2).

Preparation of M3Pyr-8,8,8

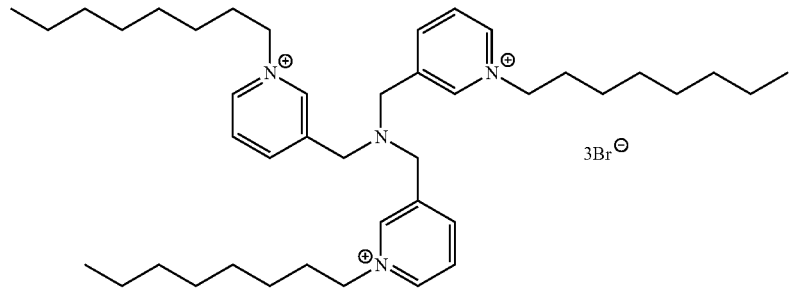 [SMILES: CCCCCCCC[n+]1cccc(CN(Cc2ccc[n+](CCCCCCCC)c2)Cc2ccc[n+](CCCCCCCC)c2)c1]

To a solution of M3Pyr (0.172 g, 0.593 mmol) in acetonitrile (1 mL) was added 1-bromooctane (0.402 g, 2.08 mmol). The resulting clear solution was heated at reflux with stirring overnight, which resulted in a beige solution. The reaction flask was cooled to room temperature, and diethyl ether (~7 mL) was added which produced a beige precipitate. The resulting crude mixture was filtered with a Büchner funnel and rinsed with diethyl ether (~10 mL), resulting in M3Pyr-8,8,8 (0.433 g, 84%) as a sticky red/orange gel; $^1$H NMR (300 MHz, CDCl$_3$) δ 9.85 (s, 3H), 8.97 (d, J=6.0 Hz, 3H), 8.83 (d, J=6.0 Hz, 3H), 8.13-8.08 (m, 3H), 4.95-4.90 (m, 6H), 4.14 (s, 6H), 1.98-1.96 (m, J=6 Hz, 6H), 1.30-1.23 (m, 30H), 0.82-0.77 (m, 6H); $^{13}$C NMR (75 MHz, CDCl$_3$) δ 146.8, 144.9, 143.1, 139.9, 128.4, 61.7, 55.6, 31.9, 31.7, 29.1, 29.0, 26.2, 22.5, 14.0; mass spectrum m/z: 314.4 ([M–H$^+$]$^{2+}$; calculated for [C$_{42}$H$_{68}$N$_4$]$^{2+}$: 314.3).

Preparation of M3Pyr-10,10,10

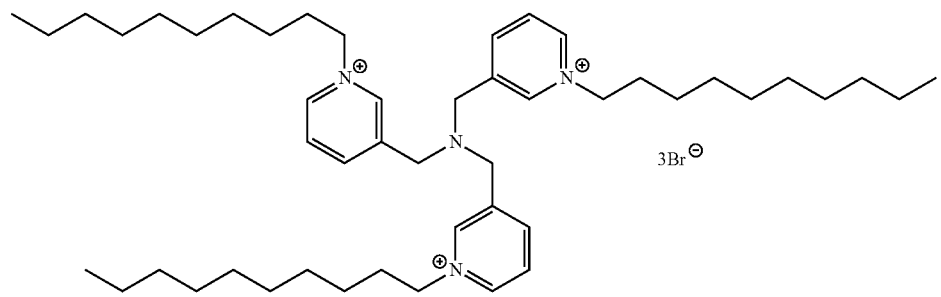 [SMILES: CCCCCCCCCC[n+]1cccc(CN(Cc2ccc[n+](CCCCCCCCCC)c2)Cc2ccc[n+](CCCCCCCCCC)c2)c1]

To a solution of M3Pyr (0.152 g, 0.524 mmol) in acetonitrile (1 mL) was added 1-bromodecane (0.404 g, 1.83 mmol). The resulting clear solution was heated at reflux with stirring overnight, which resulted in a beige solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in M3Pyr-10,10,10 (0.359 g, 72%) as a sticky red/orange gel; $^1$H NMR (300 MHz, CDCl$_3$) δ 9.93 (s, 3H), 8.99 (d, J=6.0 Hz, 3H), 8.77 (d, J=6.0 Hz, 3H), 8.11-8.06 (m, 3H), 4.96-4.92 (m, 6H), 4.18 (s, 6H), 2.98 (s, 6H), 1.32-1.13 (m, 36H), 0.86-0.81 (m, 6H); $^{13}$C NMR (75 MHz, CDCl$_3$) δ 146.8, 145.1, 142.9, 139.9, 128.3, 61.8, 55.7, 31.9, 31.8, 29.5, 29.4 29.2, 29.1, 26.2, 22.6, 13.9; mass spectrum m/z: 356.4 ([M–H$^+$]$^{2+}$; calculated for [C$_{48}$H$_{80}$N$_4$]$^{2+}$: 356.3).

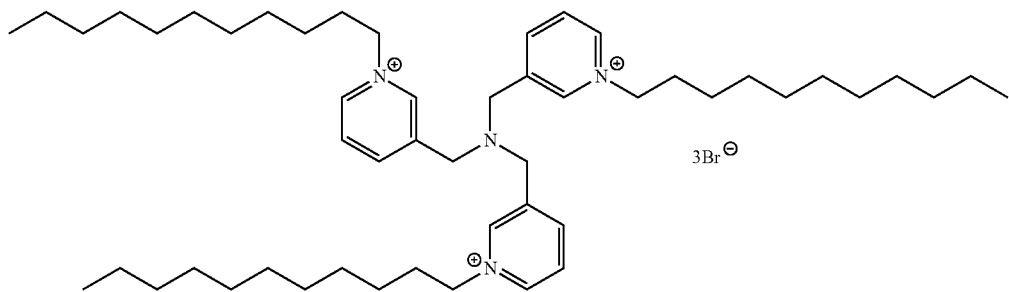 [SMILES: CCCCCCCCCCC[n+]1cccc(CN(Cc2ccc[n+](CCCCCCCCCCC)c2)Cc2ccc[n+](CCCCCCCCCCC)c2)c1]

To a solution of M3Pyr (0.150 g, 0.517 mmol) in acetonitrile (1 mL) was added 1-bromoundecane (0.404 g, 1.81 mmol). The resulting clear solution was heated at reflux with stirring overnight, which resulted in a beige solution. The reaction flask was cooled to room temperature, and diethyl ether (~7 mL) was added which produced a light yellow precipitate. The resulting crude mixture was filtered with a Büchner funnel and rinsed with diethyl ether (~10 mL), resulting in M3Pyr-11,11,11 (0.409 g, 79%) as a sticky red/orange gel; $^1$H NMR (300 MHz, CDCl$_3$) δ 9.91 (s, 3H), 8.99 (d, J=6.0 Hz, 3H), 8.74 (d, J=6.0 Hz, 3H), 8.11-8.06 (m, 3H), 4.96-4.91 (m, 6H), 4.17 (s, 6H), 1.99-1.97 (m, 6H), 1.32-1.19 (m, 42H), 0.862-0.817 (m, 6H); $^{13}$C NMR (75 MHz, CDCl$_3$) δ 146.9, 145.2, 142.8, 139.9, 128.3, 61.8, 55.7, 31.9, 31.8, 29.5, 29.4, 29.2, 29.1, 26.2, 22.6, 13.9; mass spectrum m/z: 377.4 ([M–H$^{2+}$]$^{2+}$; calculated for [C$_{51}$H$^{86}$N$_4$]$^{2+}$: 377.3).

Preparation of M3Pyr-12,12,12

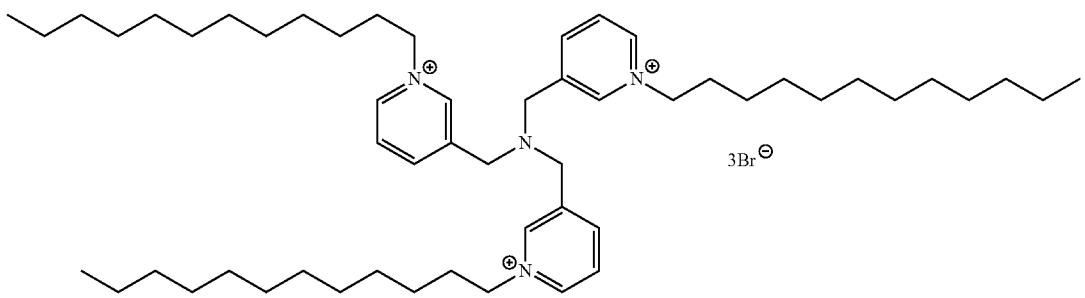 [SMILES: CCCCCCCCCCCC[n+]1cccc(CN(Cc2ccc[n+](CCCCCCCCCCCC)c2)Cc2ccc[n+](CCCCCCCCCCCC)c2)c1]

To a solution of M3Pyr (0.190 g, 0.656 mmol) in acetonitrile (1 mL) was added 1-bromododecane (0.572 g, 2.29 mmol). The resulting clear solution was heated at reflux with stirring overnight, which resulted in a beige solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in M3Pyr-12,12,12 (0.550 g, 81%) as a sticky beige crystalline solid; $^1$H NMR (300 MHz, CDCl$_3$) δ 10.1 (s, 3H), 8.99 (d, J=6.0 Hz, 3H), 8.66 (d, J=6.0 Hz, 3H), 8.06-8.01 (m, 3H), 5.01-4.95 (m, 6H), 4.23 (s, 6H), 2.05-2.00 (m, 6H), 1.34-1.22 (m, 48H), 0.887-0.866 (m, 6H); $^{13}$C NMR (75 MHz, CDCl$_3$) δ 146.8, 145.4, 142.7, 139.9, 128.2, 61.9, 55.8, 31.9, 31.8, 29.6, 29.6, 29.5, 29.4, 29.3, 29.1, 26.2, 22.6, 13.9; mass spectrum m/z: 398.4 ([M–H$^+$]$^{2+}$; calculated for [C$_{54}$H$_{92}$N$_4$]$^{2+}$: 398.4).

M3Pyr-13,13,13

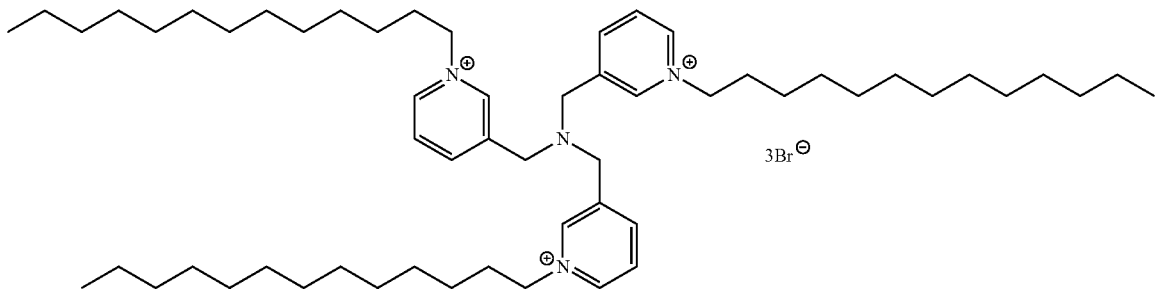 [SMILES: CCCCCCCCCCCCC[n+]1cccc(CN(Cc2ccc[n+](CCCCCCCCCCCCC)c2)Cc2ccc[n+](CCCCCCCCCCCCC)c2)c1]

To a solution of M3Pyr (0.124 g, 0.427 mmol) in acetonitrile (1 mL) was added 1-bromotridecane (0.394 g, 1.66 mmol). The resulting clear solution was heated at reflux with stirring overnight, which resulted in a beige solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in M3Pyr-13,13,13 (0.327 g, 71%) as a sticky beige solid; $^1$H NMR (300 MHz, CDCl$_3$) δ 9.91 (s, 3H), 8.98 (d, J=6.0 Hz, 3H), 8.72 (d, J=6.0 Hz, 3H), 8.10-8.06 (m, 3H), 4.96-4.91 (m, 6H), 4.17 (s, 6H), 1.99-1.97 (m, 6H), 1.30-1.21 (m, 54H), 0.879-0.834 (m, 6H); $^{13}$C NMR (75 MHz, CDCl$_3$) δ 146.8, 145.3, 142.7, 139.9, 128.2, 61.8, 55.8, 31.9, 31.8, 29.6, 29.5, 29.3, 29.2, 26.2, 22.6, 14.0; mass spectrum m/z: 419.5 ([M–H$^+$]$^{2+}$; calculated for [C$_{57}$H$_{98}$N$_4$]$^{2+}$: 419.4).

Preparation of M3Pyr-14,14,14

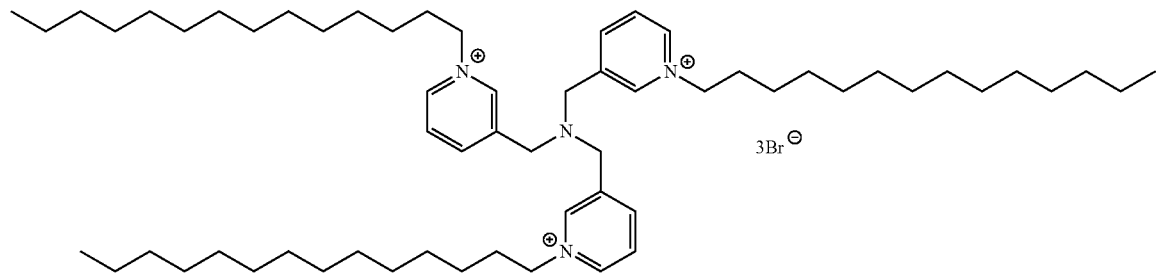 [SMILES: CCCCCCCCCCCCCC[n+]1cccc(CN(Cc2ccc[n+](CCCCCCCCCCCCCC)c2)Cc2ccc[n+](CCCCCCCCCCCCCC)c2)c1]

To a solution of M3Pyr (0.166 g, 0.574 mmol) in acetonitrile (1 mL) was added 1-bromotetradecane (0.557 g, 2.01 mmol). The resulting clear solution was heated at reflux with stirring overnight, which resulted in a beige solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in M3Pyr-14,14,14 (0.566 g, 88%) as a light pink solid; $^1$H NMR (300 MHz, CDCl$_3$) δ 9.95 (s, 3H), 8.99 (d, J=6.0 Hz, 3H), 8.74 (d, J=6.0 Hz, 3H), 8.09-8.04 (m, 3H), 4.96-4.91 (m, 6H), 4.18 (s, 6H), 1.99-1.97 (m, 6H), 1.29-1.19 (m, 60H), 0.867-0.846 (m, 6H); $^{13}$C NMR (75 MHz, CDCl$_3$) δ 146.8, 145.3, 142.8, 139.9, 128.2, 61.8, 55.8, 31.9, 31.8, 29.7, 29.6, 29.6, 29.5, 29.4, 29.4, 29.4, 29.3, 29.2, 29.1, 26.2, 22.6, 13.9; mass spectrum m/z: 440.5 ([M–H$^+$]$^{2+}$; calculated for [C$_{60}$H$_{104}$N$_4$]$^{2+}$: 440.4).

Preparation of M3Pyr-16,16,16

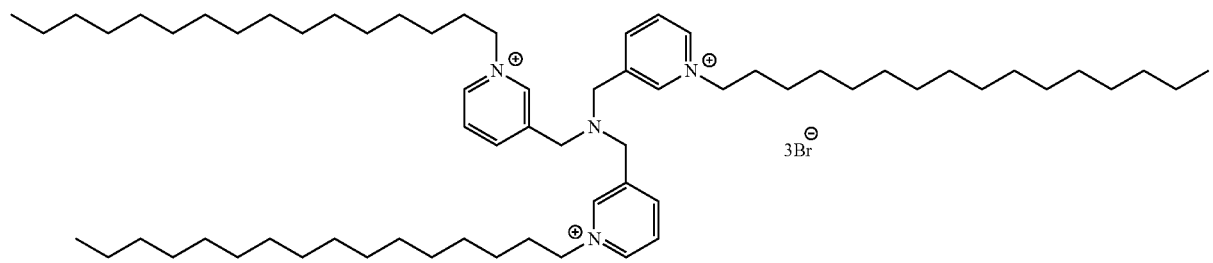 [SMILES: CCCCCCCCCCCCCCCC[n+]1cccc(CN(Cc2ccc[n+](CCCCCCCCCCCCCCCC)c2)Cc2ccc[n+](CCCCCCCCCCCCCCCC)c2)c1]

To a solution of M3Pyr (0.178 g, 0.613 mmol) in acetonitrile (1 mL) was added 1-bromohexadecane (0.657 g, 2.15 mmol). The resulting clear solution was heated at reflux with stirring overnight, which resulted in a yellow solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in M3Pyr-16,16,16 (0.716 g, 97%) as a light bisque-colored crystalline solid; mp: 148.6-153.7° C.; $^1$H NMR (300 MHz, CDCl$_3$) δ 9.96 (s, 3H), 8.98 (d, J=8.7 Hz, 3H), 8.73 (d, J=6.0 Hz, 3H), 8.08-8.06 (m, 3H), 4.94 (s, 6H), 4.17 (s, 6H), 3.40-3.36 (m, 6H), 2.00-1.99 (m, 6H), 1.30 (s, 66H), 0.850-0.828 (m, 9H); $^{13}$C NMR (75 MHz, CDCl$_3$) δ 177.5, 167.7, 163.2, 157.1, 146.8, 145.4, 142.7, 139.9, 128.1, 77.4, 76.9, 76.6, 70.8, 61.9, 56.9, 55.8, 49.6, 49.0, 33.8, 33.4, 32.8, 31.9, 29.7, 29.6, 29.5, 29.4, 29.2, 28.7, 28.1, 26.2, 25.1, 22.6, 14.0; mass spectrum m/z: 482.3 ([M−H$^+$]$^{2+}$; calculated for [C$_{66}$H$_{116}$N$_4$]$^{2+}$: 482.5).

Preparation of M3Pyr-18,18,18

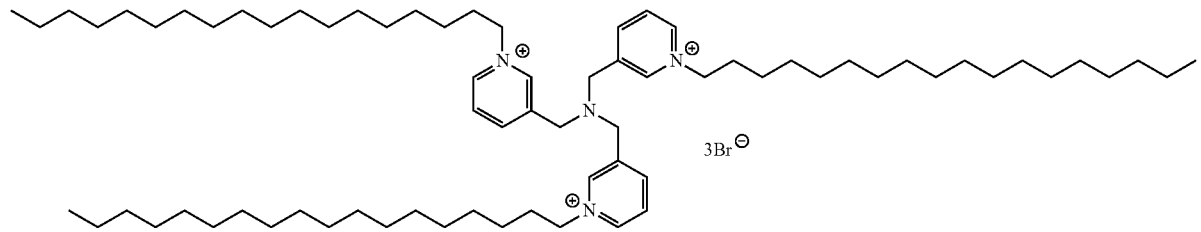 [SMILES: CCCCCCCCCCCCCCCCCC[n+]1cccc(CN(Cc2ccc[n+](CCCCCCCCCCCCCCCCCC)c2)Cc2ccc[n+](CCCCCCCCCCCCCCCCCC)c2)c1]

To a solution of M3Pyr (0.203 g, 0.699 mmol) in acetonitrile (1 mL) was added 1-bromooctadecane (0.816 g, 2.45 mmol). The resulting clear solution was heated at reflux with stirring overnight, which resulted in a yellow solution with orange precipitate. The reaction flask was cooled to room temperature, and diethyl ether (~7 mL) was added which produced a light orange precipitate. The resulting crude mixture was filtered with a Büchner funnel and rinsed with diethyl ether (~10 mL), resulting in M3Pyr-18,18,18 (0.878 g, 97%) as a light beige crystalline solid; mp: 150.3-162.4° C.; $^1$H NMR (300 MHz, CDCl$_3$) δ 10.07 (s, 3H), 8.91 (d, J=6.0 Hz, 3H), 8.34 (d, J=6.0 Hz, 3H), 7.97-7.92 (m, 3H), 4.92 (s, 6H), 4.18 (s, 6H), 3.36-3.32 (m, 6H), 1.96 (s, 3H) 1.18 (s, 84H), 0.850-0.828 (m, 9H); $^{13}$C NMR (75 MHz, CDCl$_3$) δ 146.7, 145.7, 142.6, 139.8, 137.4, 127.9, 114.5, 102.9, 69.4, 61.9, 56.1, 44.7, 33.9, 32.8, 31.9, 29.7, 29.6, 29.5, 29.5, 29.4, 29.3, 29.1, 28.8, 28.5, 28.2, 26.2, 22.6, 18.5, 14.0; mass spectrum m/z: 524.3 ([M−H$^+$]$^{2+}$; calculated for [C$_{72}$H$_{128}$N$_4$]$^{2+}$: 524.5).

Preparation of P3Pyr

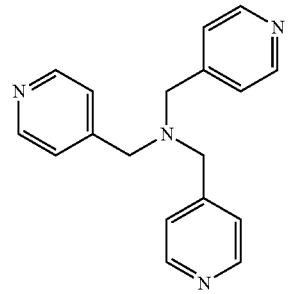 [SMILES: c1cc(CN(Cc2ccncc2)Cc2ccncc2)ccn1]

To a solution of 4-(aminomethyl)pyridine (1.48 g, 13.7 mmol) in acetic acid (5 mL) and 1,2-dichloroethane (20 mL) in an ice bath, was added sodium triacetoxyborohydride (7.29 g, 34.4 mmol) followed by 4-pyridinecarboxaldehyde (2.95 g, 27.5 mmol) with stirring. The resulting orange solution was allowed to warm to room temperature and mixed for 5 hours. The crude mixture was concentrated in vacuo, diluted with dichloromethane (30 mL), and washed twice with aqueous sodium bicarbonate (20 mL, saturated). The resulting organic solution was then washed with sodium hydroxide (10 mL, 1M) 3 times, resulting in P3Pyr (2.08 g, 52%) as a viscous brown liquid; $^1$H NMR (300 MHz, CDCl$_3$) δ 8.55 (d, J=1.8 Hz, 6.0H), 7.31 (d, J=0.7, 3H), 3.56 (s, 6H); $^{13}$C NMR (75 MHz, CDCl$_3$) δ 150.0, 147.4, 13.4, 122.8, 77.4, 76.9, 76.6, 57.3; mass spectrum m/z: 291.0 ([M+H$^+$]$^+$; calculated for [C$_{18}$H$_{19}$N$_4$]$^+$: 291.1).

Preparation of P3Pyr-10,10,10

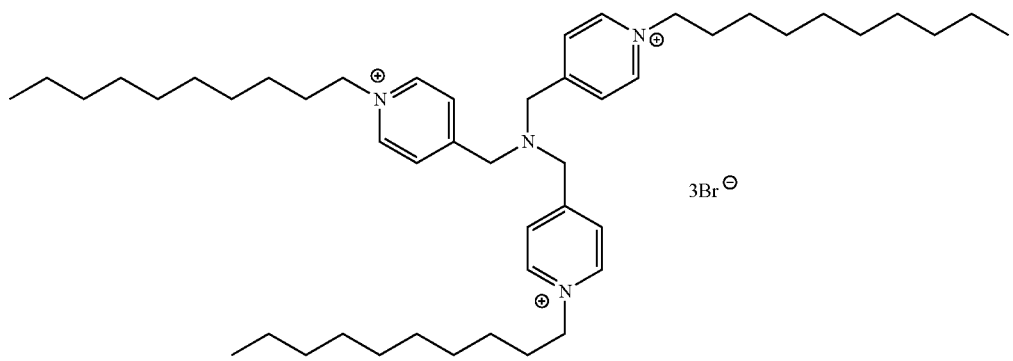 [SMILES: CCCCCCCCCC[n+]1ccc(CN(Cc2cc[n+](CCCCCCCCCC)cc2)Cc2cc[n+](CCCCCCCCCC)cc2)cc1]

To a solution of P3Pyr (0.126 g, 0.433 mmol) in acetonitrile (1 mL) was added 1-bromodecane (0.287 g, 1.29 mmol). The resulting yellow solution was heated at reflux with stirring overnight, which resulted in a black solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in P3Pyr-10,10,10 (0.365 g, 88%) as a dark red gel; $^1$H NMR (300 MHz, CDCl$_3$) δ 8.99 (d, J=6.0 Hz, 6H), 8.56 (d, J=6.0 Hz, 6H), 4.59-4.57 (m, 6H), 4.22 (s, 6H), 1.25-1.16 (m, 48H), 0.811-0.768 (s, 9H); $^{13}$C NMR (75 MHz, CDCl$_3$) δ 158.6, 144.4, 128.9, 31.8, 31.5, 29.4, 29.3, 29.2, 29.0, 26.2, 22.6; mass spectrum m/z: 286.3 ([M-C$_{10}$H$_{21}$]$^{2+}$; calculated for [C$_{38}$H$_{60}$N$_4$]$^{2+}$: 286.3).

Preparation of P3Pyr-12,12,12

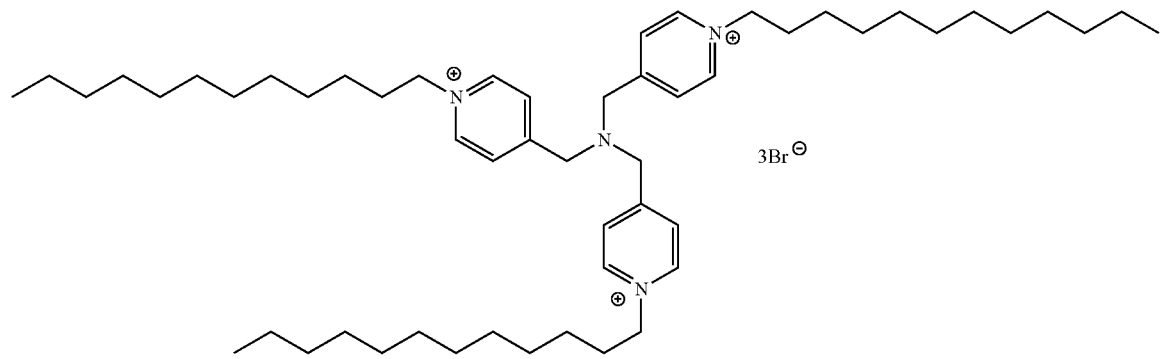 [SMILES: CCCCCCCCCCCC[n+]1ccc(CN(Cc2cc[n+](CCCCCCCCCCCC)cc2)Cc2cc[n+](CCCCCCCCCCCC)cc2)cc1]

To a solution of P3Pyr (0.131 g, 0.451 mmol) in acetonitrile (1 mL) was added 1-bromododecane (0.338 g, 1.36 mmol). The resulting yellow solution was heated at reflux with stirring overnight, which resulted in a black solution. The reaction flask was cooled to room temperature, and diethyl ether (~7 mL) was added which produced a light beige precipitate. The resulting crude mixture was filtered with a Büchner funnel and rinsed with diethyl ether (~10 mL), resulting in P3Pyr-12,12,12 (0.369 g, 78%) as a dark red gel; $^1$H NMR (300 MHz, CDCl$_3$) δ 9.02 (d, J=6.0 Hz, 6H), 8.65 (d, J=6.0 Hz, 6H), 4.67-4.62 (m, 6H), 4.30 (s, 6H), 1.31-1.22 (m, 60H), 0.877-0.834 (s, 9H); $^{13}$C NMR (75 MHz, CDCl$_3$) δ 177.9, 158.5, 144.4, 128.9, 61.6, 31.8, 31.5, 29.5, 29.4, 29.3, 29.0, 26.2, 22.6, 15.2, 14.0; mass spectrum m/z: 314.4 ([M-C$_{12}$H$_{25}$]$^{2+}$; calculated for [C$_{42}$H$_{68}$N$_4$]$^{2+}$: 314.3).

Biological Assays

For all biological assays, laboratory strains of methicillin-susceptible *Staphylococcus aureus* MSSA (SH1000), *Enterococcus faecalis* (OG1RF), *Escherichia coli* (MC4100), *Pseudomonas aeruginosa* (PAO1), community-acquired methicillin-resistant *Staphylococcus aureus* CA-MRSA (USA300-0114), and hospital-acquired methicillin-resistant *Staphylococcus aureus* HA-MRSA (ATCC 33591) were grown with shaking at 37° C. overnight from freezer stocks in 10 mL of the indicated media.

Minimum Inhibitory Concentration (MIC)

Compounds were serially diluted two-fold from stock solutions to yield twelve test concentrations. Overnight *S. aureus, E. faecalis, E. coli, P. aeruginosa*, USA300-0114 (CA-MRSA), and ATCC 33591 (HA-MRSA) cultures diluted to ca. 10$^6$ cfu/mL in MH media and 100 µL were inoculated into each well of a U-bottom 96-well plate (BD Biosciences, BD 351177) containing 100 µL of compound solution. Plates were incubated statically at 37° C. for 72 hours upon which time wells were evaluated visually for bacterial growth. The MIC was determined as the lowest concentration of compound resulting in no bacterial growth visible to the naked eye, based on the majority of three independent experiments. Aqueous DMSO controls were conducted as appropriate for each compound.

Red Blood Cell (RBC) Lysis Assay (Lysis$_{20}$)

RBC lysis assays were performed on mechanically defibrinated sheep blood (Hemostat Labs: DSB030). 1.5 mL of blood was placed into a microcentrifuge tube and centrifuged at 10,000 rpm for ten minutes. The supernatant was removed and the cells were resuspended with 1 mL of phosphate-buffered saline (PBS). The suspension was centrifuged as previously, the supernatant was removed, and cells were resuspended two more times. The final cell suspension was diluted twentyfold with PBS. The twenty-fold suspension dilution was then aliquoted into microcentrifuge tubes containing compound serially diluted in PBS. TritonX (1% by volume) served as a positive control (100% lysis marker) and sterile PBS served as a negative control (0% lysis marker). Samples were then placed in an incubator at 37.0 and shaken at 200 rpm. After 1 hour, the samples were centrifuged at 10,000 rpm for ten minutes. The absorbance of the supernatant was measured with a UV spectrometer at a 540 nm wavelength.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound selected from the group consisting of formula I-IV:

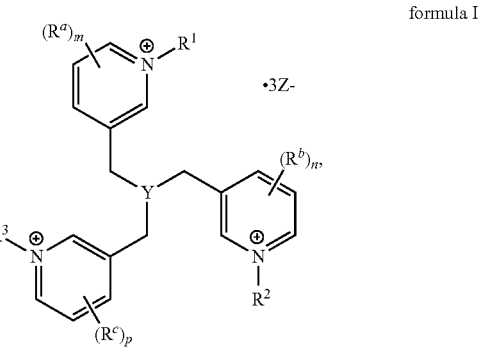

formula I formula II

[Structure of formula II: tripyridinium compound with Y center, substituents $(R^a)_m$, $(R^b)_n$, $(R^c)_p$, $R^1$, $R^2$, $R^3$, ·3Z−]

formula III

[Structure of formula III: tripyridinium compound with Y center, ortho-substituted pyridines, ·3Z−]

formula IV

[Structure of formula IV: bis-pyridinium ethane-type compound with $R^c$, $R^d$, $R^e$ on the central carbons, $(R^a)_m$, $(R^b)_n$, $R^1$, $R^2$, ·2Z−]

wherein in formula I-III:

$R^1$, $R^2$, and $R^3$ are each independently selected from the group consisting of H or $C_1$-$C_{25}$ alkyl, wherein the alkyl group may be optionally substituted with —OR', —NR'$_2$, —NR'—C(O)R', —C(O)NR'$_2$, —NR'—C(O) CR'=CR', —SR', —O—C(O)R', —C(O)OR', —C(O) R', —CF$_3$, —OCF$_3$, halogen, benzyl, o-vinylbenzyl, m-vinylbenzyl, p-vinylbenzyl, phenyl, allyl, and substituted allyl, further wherein the alkyl group may optionally be interrupted with a —O—C(O)— group or a —C(O)O— group;

each occurrence of $R^a$, $R^b$, $R^c$, $R^d$, and $R^e$ is independently selected from the group consisting of H, $C_1$-$C_6$ alkyl, —OR', —CN, —NO$_2$, —NR'$_2$, —N—C(O)R', —C(O) NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and $C_{1-4}$ alkyl;

Y is N;

each occurrence of Z− is independently selected from the group consisting of Br− and I−;

m is an integer from 0 to 4;

n is an integer from 0 to 4; and p is an integer from 0 to 4; and wherein in formula IV:

$R^1$ and $R^2$ are each independently selected from the group consisting of H or $C_1$-$C_{25}$ alkyl, wherein the alkyl group may be optionally substituted with —OR', —NR'$_2$, —NR'—C(O)R', —C(O)NR'$_2$, —NR'—C(O) CR'=CR', —SR', —O—C(O)R', —C(O)OR', —C(O) R', —CF$_3$, —OCF$_3$, halogen, benzyl, o-vinylbenzyl, m-vinylbenzyl, p-vinylbenzyl, phenyl, allyl, and substituted allyl, further wherein the alkyl group may optionally be interrupted with a —O—C(O)— group or a —C(O)O— group, and each occurrence of Z− is I− when $R^1$ and $R^2$ are $C_{12}$ alkyl;

each occurrence of $R^a$ and $R^b$ is independently selected from the group consisting of $C_1$-$C_6$ alkyl, —OR', —CN, —NO$_2$, —NR'$_2$, —N—C(O)R', —C(O)NR'$_2$, —N—C(O)CR'=CR', —SR', —O—C(O)R', —C(O) OR', —C(O)R', —CF$_3$, —OCF$_3$, and halogen; when each occurrence of $R^c$, $R^d$, and $R^e$ is independently selected from the group consisting of H, $C_1$-$C_6$ alkyl, —OR', —CN, —NO$_2$, —NR'$_2$, —N—C(O)R', —C(O) NR'$_2$, —N—C(O)CR'=CR', —SR', —O—C(O)R', —C(O)OR', —C(O)R', —CF$_3$, —OCF$_3$, and halogen; or each occurrence of $R^a$ and $R^b$ is independently selected from the group consisting of H, $C_1$-$C_6$ alkyl, —OR', —CN, —NO$_2$, —NR'$_2$, —N—C(O)R', —C(O)NR'$_2$, —N—C(O)CR'=CR', —SR', —O—C(O)R', —C(O) OR', —C(O)R', —CF$_3$, —OCF$_3$, and halogen; when each occurrence of $R^c$, $R^d$, and $R^e$ is independently selected from the group consisting of $C_1$-$C_6$ alkyl, —OR', —CN, —NO$_2$, —NR'$_2$, —N—C(O)R', —C(O) NR'$_2$, —N—C(O)CR'=CR', —SR', —O—C(O)R', —C(O)OR', —C(O)R', —CF$_3$, —OCF$_3$, and halogen;

each occurrence of R' is independently selected from the group consisting of H and $C_{1-4}$ alkyl;

each occurrence of Z− is independently selected from the group consisting of Br− and I−;

m is an integer from 0 to 4; and n is an integer from 0 to 4.

2. The compound of claim 1, wherein in formula I-III at least one of $R^1$, $R^2$, and $R^3$ is selected from the group consisting of $C_8$ alkyl, $C_{10}$ alkyl, $C_{11}$ alkyl, $C_{12}$ alkyl, $C_{13}$ alkyl, $C_{14}$ alkyl, $C_{16}$ alkyl, and $C_{18}$ alkyl; and wherein in formula IV at least one of $R^1$ and $R^2$ is selected from the group consisting of $C_8$ alkyl, $C_{10}$ alkyl, $C_{11}$ alkyl, $C_{13}$ alkyl, $C_{14}$ alkyl, $C_{16}$ alkyl, and $C_{18}$ alkyl.

3. The compound of claim 1, wherein the $R^1$, $R^2$, and $R^3$ are each independently selected from the group consisting of —$R^4$—O—C(O)—$R^5$ and —$R^4$—(O)C—O—$R^5$, wherein $R^4$ and $R^5$ are each independently an optionally substituted alkyl chain, provided that the total number of carbon atoms in the alkyl chains of $R^4$ and $R^5$ is 4 to 25 carbon atoms.

4. The compound of claim 1, wherein Z− is Br−.

5. The compound of claim 1, wherein in formula I-III: $R^1$, $R^2$, and $R^3$ are each $C_8$-$C_{18}$ alkyl; and wherein in formula IV: $R^1$ and $R^2$ are each $C_8$-$C_{11}$ or $C_{13}$-$C_{18}$ alkyl.

6. The compound of claim 1, wherein the compound is selected from the group consisting of:

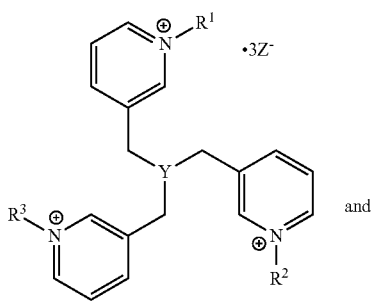

M3Pyr-8,8,8 - R¹, R², R³ = $C_8H_{17}$
M3Pyr-10,10,10 - R¹, R², R³ = $C_{10}H_{21}$
M3Pyr-11,11,11 - R¹, R², R³ = $C_{11}H_{23}$
M3Pyr-12,12,12 - R¹, R², R³ = $C_{12}H_{25}$
M3Pyr-13,13,13 - R¹, R², R³ = $C_{13}H_{27}$
M3Pyr-14,14,14 - R¹, R², R³ = $C_{14}H_{29}$
M3Pyr-16,16,16 - R¹, R², R³ = $C_{16}H_{33}$
M3Pyr-18,18,18 - R¹, R², R³ = $C_{18}H_{37}$ and

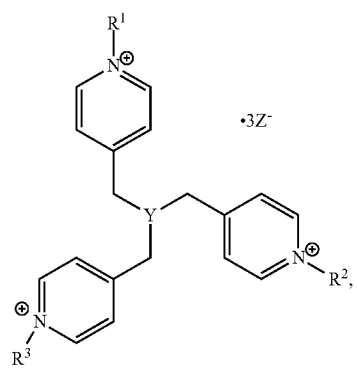

P3Pyr-8,8,8 - R¹, R², R³ = $C_8H_{17}$
P3Pyr-10,10,10 - R¹, R², R³ = $C_{10}H_{21}$
P3Pyr-11,11,11 - R¹, R², R³ = $C_{11}H_{23}$
P3Pyr-12,12,12 - R¹, R², R³ = $C_{12}H_{25}$
P3Pyr-13,13,13 - R¹, R², R³ = $C_{13}H_{27}$
P3Pyr-14,14,14 - R¹, R², R³ = $C_{14}H_{29}$
P3Pyr-16,16,16 - R¹, R², R³ = $C_{16}H_{33}$
P3Pyr-18,18,18 - R¹, R², R³ = $C_{18}H_{37}$ wherein each occurrence of Z⁻ is independently selected from the group consisting of I⁻ and Br⁻.

7. The compound of claim 1, wherein the at least one compound is bound to a second compound or moiety selected from the group consisting of a QAC, an antimicrobial peptide, a sugar, an iron siderophore, a solid surface, a poly(alkyl ether), and a nucleophilic residue.

8. A compound selected from the group consisting of formula I-IV:

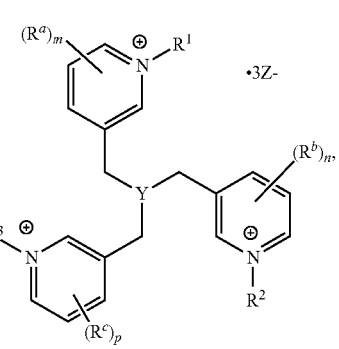

formula I

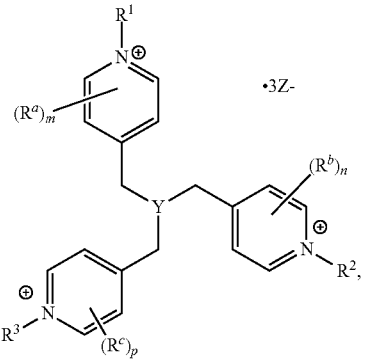

formula II

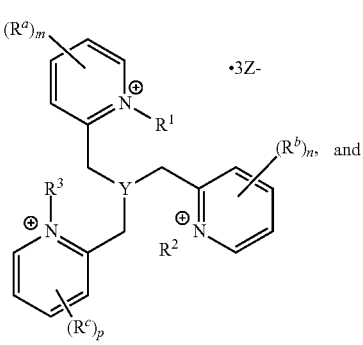

formula III

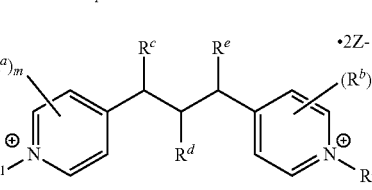

formula IV wherein in formula I-III:
R¹, R², and R³ are each independently selected from the group consisting of H or $C_1$-$C_{25}$ alkyl, wherein the alkyl group may be optionally substituted with —OR', —NR'₂, —NR'—C(O)R', —C(O)NR'₂, —NR'—C(O)CR'=CR', —SR', —O—C(O)R', —C(O)OR', —C(O)R', —CF₃, —OCF₃, halogen, benzyl, o-vinylbenzyl, m-vinylbenzyl, p-vinylbenzyl, phenyl, allyl, and substituted allyl, further wherein the alkyl group may optionally be interrupted with a —O—C(O)— group or a —C(O)O— group;
each occurrence of $R^a$, $R^b$, $R^c$, $R^d$, and $R^e$ is independently selected from the group consisting of H, $C_1$-$C_6$ alkyl, —OR', —CN, —NO₂, —NR'₂, —N—C(O)R', —C(O)NR'₂, —N—C(O)CR'=CR', —SR', —O—C(O)R', —C(O)OR', —C(O)R', —CF₃, —OCF₃, and halogen;
each occurrence of R' is independently selected from the group consisting of H and $C_{1-4}$ alkyl;

Y is N;

each occurrence of $Z^-$ is independently selected from the group consisting of $Br^-$ and $I^-$;

m is an integer from 0 to 4;

n is an integer from 0 to 4; and p is an integer from 0 to 4; and wherein in formula IV:

$R^1$ and $R^2$ are each independently selected from the group consisting of —$R^4$—O—C(O)—$R^5$ and —$R^4$—(O)C—O—$R^5$, wherein $R^4$ and $R^5$ are each independently an optionally substituted alkyl chain, provided that the total number of carbon atoms in the alkyl chains of $R^4$ and $R^5$ is 4 to 25 carbon atoms;

each occurrence of $R^a$ and $R^b$ is independently selected from the group consisting of $C_1$-$C_6$ alkyl, —OR', —CN, —$NO_2$, —NR'$_2$, —N—C(O)R', —C(O)NR'$_2$, —N—C(O)CR'═CR', —SR', —O—C(O)R', —C(O)OR', —C(O)R', —$CF_3$, —$OCF_3$, and halogen; when each occurrence of $R^c$, $R^d$, and $R^e$ is independently selected from the group consisting of H, $C_1$-$C_6$ alkyl, —OR', —CN, —$NO_2$, —NR'$_2$, —N—C(O)R', —C(O)NR'$_2$, —N—C(O)CR'═CR', —SR', —O—C(O)R', —C(O)OR', —C(O)R', —$CF_3$, —$OCF_3$, and halogen; or each occurrence of $R^a$ and $R^b$ is independently selected from the group consisting of H, $C_1$-$C_6$ alkyl, —OR', —CN, —$NO_2$, —NR'$_2$, —N—C(O)R', —C(O)NR'$_2$, —N—C(O)CR'═CR', —SR', —O—C(O)R', —C(O)OR', —C(O)R', —$CF_3$, —$OCF_3$, and halogen; when each occurrence of $R^c$, $R^d$, and $R^e$ is independently selected from the group consisting of $C_1$-$C_6$ alkyl, —OR', —CN, —$NO_2$, —NR'$_2$, —N—C(O)R', —C(O)NR'2, —N—C(O)CR'═CR', —SR', —O—C(O)R', —C(O)OR', —C(O)R', —$CF_3$, —$OCF_3$, and halogen; and each occurrence of R' is independently selected from the group consisting of H and $C_{1-4}$ alkyl;

each occurrence of $Z^-$ is independently selected from the group consisting of $Br^-$ and $I^-$;

m is an integer from 0 to 4; and n is an integer from 0 to 4.

* * * * *

UNITED STATES PATENT AND TRADEMARK OFFICE
CERTIFICATE OF CORRECTION

| | | |
|---|---|---|
| PATENT NO. | : 11,111,216 B2 | Page 1 of 1 |
| APPLICATION NO. | : 16/343418 | |
| DATED | : September 7, 2021 | |
| INVENTOR(S) | : William M. Wuest et al. | |

It is certified that error appears in the above-identified patent and that said Letters Patent is hereby corrected as shown below:

In the Specification

Column 1, Line 15 should read as follows:
STATEMENT REGARDING FEDERALLY SPONSORED RESEARCH OR DEVELOPMENT
This invention was made with government support under DGE1144462 awarded by the National Science Foundation. The government has certain rights in the invention.

Signed and Sealed this
Seventeenth Day of September, 2024

Katherine Kelly Vidal
*Director of the United States Patent and Trademark Office*